US012560611B2

(12) United States Patent
Fischer

(10) Patent No.: US 12,560,611 B2
(45) Date of Patent: Feb. 24, 2026

(54) RATIO BETWEEN PLGF AND sFLt1 IS PREDICTIVE FOR NEURAL INVASION IN PATIENTS SUFFERING FROM PANCREATIC CANCER

(71) Applicant: CHARITÉ-UNIVERSITAETSMEDIZIN BERLIN, Berlin (DE)

(72) Inventor: Christian Fischer, Berlin (DE)

(73) Assignee: CHARITE—UNIVERSITAETSMEDIZIN BERLIN, Berlin (DE)

( * ) Notice: Subject to any disclaimer, the term of this patent is extended or adjusted under 35 U.S.C. 154(b) by 638 days.

(21) Appl. No.: 18/000,989

(22) PCT Filed: Jul. 8, 2021

(86) PCT No.: PCT/EP2021/068971
§ 371 (c)(1),
(2) Date: Dec. 7, 2022

(87) PCT Pub. No.: WO2022/008648
PCT Pub. Date: Jan. 13, 2022

(65) Prior Publication Data
US 2023/0375553 A1 Nov. 23, 2023

(30) Foreign Application Priority Data
Jul. 10, 2020 (EP) .................................... 20185174

(51) Int. Cl.
*G01N 33/574* (2006.01)
*A61K 39/00* (2006.01)

(52) U.S. Cl.
CPC .... *G01N 33/57438* (2013.01); *A61K 39/0011* (2013.01); *A61K 2039/5156* (2013.01); *G01N 2333/71* (2013.01); *G01N 2333/91215* (2013.01); *G01N 2800/52* (2013.01)

(58) Field of Classification Search
CPC ......... G01N 33/57438; G01N 2333/71; G01N 2800/52; A61K 39/0011; A61K 39/395; C07K 2317/76; C07K 16/22
See application file for complete search history.

(56) References Cited

U.S. PATENT DOCUMENTS 4,675,187 A 6/1987 Konishi et al.

FOREIGN PATENT DOCUMENTS

EP 1869085 A2 12/2007

OTHER PUBLICATIONS

Fischer (Cell 2007 131:463-475). (Year: 2007).*
Göhrig Andreas et al: "Placental growth factor promotes neural invasion and predicts disease prognosis in resectable pancreatic cancer", Journal of Experimental & Clinical Cancer Research, vol. 43, No. 1, May 30, 2024 (May 30, 2024).
Office Action issued on Nov. 22, 2024 in Application No. EP21742112.2.
Georg Hilfenhaus et al: "Placental growth factor supports neuroendocrine tumor growth and predicts disease prognosis in patients", Endocrine Related Cancer, vol. 20, No. 3, Mar. 5, 2013, pp. 305-319.
International Search Report in PCT/EP2021/068971 mailed on Sep. 20, 2021.
D Liang et al: "New insights into perineural invasion of pancreatic cancer: More than pain" , Biochimica Et Biophysica Acta, Jan. 1, 2016, pp. 111-122.
Yu-Ting Chang et al: "Serum Vascular Endothelial Growth Factor/Soluble Vascular Endothelial Growth Factor Receptor 1 Ratio Is an Independent Prognostic Marker in Pancreatic Cancer", Pancreas, vol. 37, No. 2, Aug. 1, 2008; pp. 145-150.

* cited by examiner

*Primary Examiner* — Changhwa J Cheu
(74) *Attorney, Agent, or Firm* — FOX ROTHSCHILD LLP

(57) ABSTRACT

The present invention is directed to a method for identifying neural invasion in a pancreatic cancer patient, the method comprising the steps of: determining in a sample of a pancreatic cancer patient the expression level of PlGF and sFlt1; and calculating a ratio of the expression levels of PlGF and sFlt1, wherein the expression level of PlGF forms part either of the numerator or of the denominator of the ratio; characterized in that, a deviation of the ratio of the patient sample from a reference sample or a predetermined threshold value is indicative for presence of neural invasion of the pancreatic cancer in said patient. Preferably said deviation, when the ratio is expressed using the expression level of PlGF in the numerator, is an increase in the ratio of the patient sample compared to a reference sample or a predetermined threshold value and/or said deviation, when the ratio is expressed using the expression level of PlGF in the denominator, is a decrease in the ratio of the patient sample compared to a reference sample or a predetermined threshold value.

16 Claims, 14 Drawing Sheets

Figure 1:
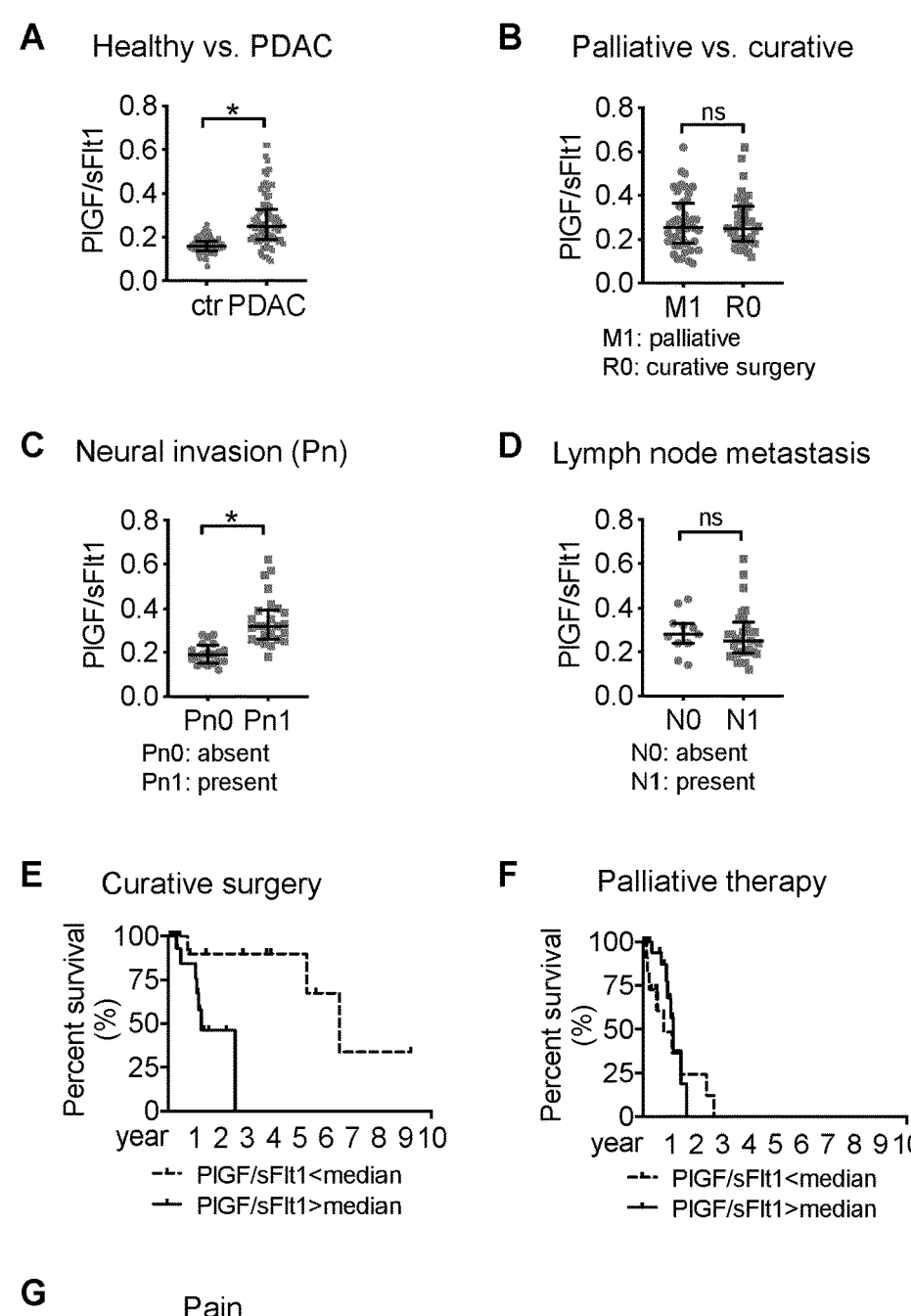

Specification includes a Sequence Listing.

A  macrophages    B  fibroblasts human PDAC

C    D

RATIO BETWEEN PLGF AND sFLt1 IS PREDICTIVE FOR NEURAL INVASION IN PATIENTS SUFFERING FROM PANCREATIC CANCER

CROSS-REFERENCE TO RELATED APPLICATIONS

This application is a § 371 national phase entry of International Patent Application No. PCT/EP2021/068971 filed on Jul. 8, 2021, which claims priority to and the benefit of European Patent Application No. 20185174.8 filed on Jul. 10, 2020, both of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created on May 12, 2023, is named 3975-183_157361_09301_SL.txt and is 9,174 bytes in size.

BACKGROUND OF THE INVENTION

Pancreatic ductal adenocarcinoma (PDAC) currently represents the fourth leading cause of cancer-related deaths in the Western world and is projected to become the second leading cause (of cancer-related deaths) before 2030. PDAC is frequently detected in a disseminated and hence unresectable stage with median survival of 4-6 months under palliative chemotherapy and an overall 5-year survival rate below 5%. Tumor resection improves median survival up to 20 months, but almost all patients undergoing surgery will experience early disease recurrence. Early metastatic spread of PDAC cells via (lymph)-vessels and in particular along nerves accounts for the high recurrence rates, as nodal involvement and neural invasion have long been recognized as adverse prognostic factors.

Neural invasion (NI) has emerged as a key pathologic feature of PDAC and represents a distinct route of tumor cell spread independent from lymphatic and hematogenous tumor cell dissemination. NI is associated with an unfavourable course of the disease, and also constitutes a major cause of neuropathic pain, which is difficult to treat, thus limiting the quality of life. Molecular and cellular determinants of NI are slowly starting to unravel. Current concepts of NI emphasize the reciprocal interaction between tumor cells and nerves in a process driven by mutual attraction, resulting in axonal outgrowth of neurites towards the tumor cells and tumor cell invasion along pathways charted by neurons and ensheathing Schwann cells. Indeed, neural hypertrophy and increased nerve densities are observed in PDAC, indicating that interaction of tumor cells with nerves affects neural morphology and plasticity. Neurotrophins, cytokines as well as membrane bound cell surface ligands and respective counter-receptors have been implicated in NI. More recently, pancreatic stellate cells, macrophages and Schwann cells have become a focus of interest, as they turn into a source of neurotrophic and chemoattractant factors when activated.

Axon guidance factors and their receptors exhibit features which uniquely qualify them as attractive candidate regulators of NI in PDAC. Physiologically, axon guidance factors function as signalling cues to direct outgrowth, navigation and positioning of neurons in the developing brain. As evolution progressed, ancient axon guidance systems were co-opted for navigation of the emerging blood vessels. Conversely, VEGF, which was originally discovered as a major angiogenic growth factor, has recently been characterized as neurotrophic factor in brain development and motoneuron diseases and furthermore implicated in neural remodelling under pathophysiological conditions of neuropathic pain.

Slit2 and its Robo receptors constitute such repellent axon and vessel guidance factors that exhibit frequent genetic alteration in PDAC. Own data revealed that disruption of Slit2-Robo activity in PDAC facilitates bidirectional chemoattraction of tumor cells with neural cell, and more specifically fosters unidirectional PDAC cell navigation along outgrowing neurites in models of neural invasion, hence creating precedent evidence for a functional role of axon guidance factor in NI of PDAC.

Starting from this concept of the neurovascular link, we currently explored the role of placental growth factor (PlGF) for tumor-specific mechanisms of metastatic progress in PDAC. PlGF has originally been characterized as an angiogenic growth factor of the VEGF family, which binds the VEGF receptor-1 (VEGFR1) and Neuropilin-1 (Nrp1). Own studies revealed that PlGF is redundant for physiological vessel growth, but substantially contributes to pathological angiogenesis. Accordingly, PlGF expression is hardly detectable under healthy conditions, but increased in malignancies, in which tumor and/or circulating PlGF levels correlated with vascularity, metastasis, tumor recurrence and patient survival. Mechanistically, PlGF functions as a pleiotropic cytokine that is expressed by and affects a wide range of different cell types within the tumor microenvironment. Thus, PlGF stimulates endothelial cell migration and growth, and recruits smooth muscle cells, tumor associated macrophages (TAMs) and other angiogenesis-competent bone marrow derived progenitors. Most recently, the axon guidance receptor, neuropilin-1 (Nrp1) was found to acts as independent receptor for PlGF and conveys signals different from established VEGFR1-mediated signaling pathways. Interestingly, high expression of Nrp1 was associated with poor overall survival in patients following resection of PDAC.

Compared to VEGF, the role of PlGF for nerve wiring in the nervous system is less understood, but likely restricted to pathological conditions, analogous to its redundant role in physiological angiogenesis. Indeed, induction of PlGF in neurons and vascular cells reduced ischemia induced cortical lesion size and functional deficits and protected from retinal neural cell damage. Moreover, injury of peripheral nerves caused induction of PlGF in Schwann cells, which in turn stimulated axonal regrowth, whereas loss of PlGF in PlGF−/− mice accelerated Wallerian degeneration. Intramuscular PlGF gene delivery in diabetic mice furthermore ameliorated sensory neuropathy by promoting regeneration of nerve fibers. To date, neither expression nor function of PlGF in human PDAC biology has been studied in detail.

Thus, there is a substantial medical need for means and methods to objectively and reproducibly identify or diagnose neural invasion in subjects suffering from pancreatic cancer as well as in treatment options tailored to disease courses depending on the presence and amount of neural invasion in individual pancreatic cancer patients.

DESCRIPTION OF THE INVENTION

The present invention is directed to a method for identifying neural invasion in a pancreatic cancer patient, the method comprising the steps of:

determining in a sample of a pancreatic cancer patient the expression level of PlGF and sFLT-1; and calculating a ratio of the expression levels of PlGF and sFlt1, wherein the expression level of PlGF forms part either of the numerator or of the denominator of the ratio;

wherein, a deviation of the ratio of the patient sample from a reference sample or a predetermined threshold value is indicative for presence of neural invasion of the pancreatic cancer in said patient.

Preferably, said deviation, when the ratio is expressed using the expression level of PlGF in the numerator, is an increase in the ratio of the patient sample compared to a reference sample or a predetermined threshold value and/or said deviation, when the ratio is expressed using the expression level of PlGF in the denominator, is a decrease in the ratio of the patient sample compared to a reference sample or a predetermined threshold value.

It should be noted that the method of the present invention encompasses a ratio of expression levels of PlGF and sFlt1, wherein the expression level of PlGF forms either part of the numerator or of the denominator. However, for ease of reference, and since such a ratio can easily be expressed as the respective reciprocal ratio, the invention is explained with reference to a ratio, wherein the ratio is expressed using the expression level of PlGF in the numerator. It should be understood that for cases wherein the ratio is calculated using the expression level of PlGF in the denominator, comparison has to be made to the respective reciprocal threshold values and the ratio will be informative if said ratio of a patient sample decreases said reciprocal threshold value or ratio of a reference sample. In other words, the method of the present invention can be characterized in that, when the ratio is expressed using the expression level of PlGF in the denominator, a decrease in the ratio of the patient sample compared to a reference sample or a predetermined threshold value (which is reciprocal to the threshold value used for ratio wherein the expression level of PlGF is used in the numerator) is indicative for presence of neural invasion of the pancreatic cancer in said patient.

The present invention is based on the unexpected fact that a ratio of the expression levels of the two soluble and circulating factors PlGF and sFlt1 is correlated with presence and extent of neural invasion of pancreatic tumor cells in patients suffering from pancreatic cancer, wherein, when the ratio is expressed using the expression level of PlGF in the numerator, an increase in the ratio is informative, and when the ratio is expressed using the expression level of PlGF in the denominator, a decrease in the ratio is informative. This correlation allows for prediction not only whether a particular pancreatic cancer patient already suffers from neural invasion but allows also for prediction of incidence and extent of extra-tumoral neural invasion (i.e. invasion of nerves and neural tissue outside the primary pancreatic tumor), disease prognosis and overall survival The present invention is directed to patients suffering from pancreatic cancer. For the purpose of the present invention, the term "pancreatic cancer" is used in its art recognized meaning. Pancreatic cancer arises when cells in the pancreas begin to multiply out of control and form a mass. These cancerous cells have the ability to invade other parts of the body. There are a number of types of pancreatic cancer. The most common, pancreatic adenocarcinoma, accounts for about 90% of cases. These adenocarcinomas start within the part of the pancreas which makes digestive enzymes. Several other types of cancer, which collectively represent the majority of the non-adenocarcinomas, can also arise from these cells. One to two percent of cases of pancreatic cancer are neuroendocrine tumors, which arise from the hormone-producing cells of the pancreas. These are generally less aggressive than pancreatic adenocarcinoma. For the purpose of the present invention, the term "pancreatic cancer" refers to all types of pancreatic cancer, wherein pancreatic adenocarcinoma or pancreatic ductal adenocarcinoma (PDAC) is a preferred type of pancreatic cancer.

For the purpose of the present invention, the terms "patient" or "subject" refer to a mammal, including but not limited to, a human or non-human mammal, such as a bovine, equine, canine, ovine, or feline. Preferably the patient or subject is a human. In a preferred embodiment of the method of the invention, the pancreatic cancer patient has not yet undergone partial or full resection of said pancreatic cancer or parts thereof.

In the method of the invention, the expression levels of PlGF and sFlt1 are determined in a sample of a pancreatic cancer patient.

By "placental growth factor (PlGF)" is meant a mammalian growth factor that is homologous to the protein defined by GenBank accession number P49763 and that has PlGF biological activity. PlGF is a glycosylated homodimer belonging to the VEGF family and can be found in two distinct isoforms through alternative splicing mechanisms. As a growth factor, PlGF represents a soluble polypeptide which is circulating in body fluids.

By "soluble Flt1 (sFlt1)" (also known as sVEGF-R1) is meant the soluble form of the Flt1 receptor, that is homologous to the protein defined by GenBank accession number U01134, and that has sFlt1 biological activity. The biological activity of sFlt1 polypeptide may be assayed using any standard method, for example, by assaying sFlt1 binding to VEGF. sFlt1 lacks the transmembrane domain and the cytoplasmic tyrosine kinase domain of the Flt-1 receptor. sFlt1 can bind to VEGF and PlGF. As used herein, sFlt1 includes any sFlt1 family member or isoform.

In the method of the invention, expression levels or expression amount can be determined based on any suitable criterion known in the art, including but not limited to mRNA, cDNA, and/or polypeptide. Expression levels/amounts can be determined quantitatively or semi-quantitatively. In the method of the invention, expression levels can be determined in absolute quantity or normalized to an adequate base. In case expression levels are determined on the basis of mRNA or cDNA, an adequate base may be the total amount or RNA or cDNA assayed. Alternatively, normalization may occur with reference to a normalizing gene, RNA or cDNA like a housekeeping gene such as GAPDH. Alternatively, normalization can be based on the mean or median signal of all of the assayed genes or a large subset thereof (global normalization approach). In case expression levels are determined on basis of polypeptide, an adequate base may be the amount of detected polypeptide in relation to the total amount of the sample, e.g. in weight/weight (e.g. in ng/mg) or weight per volume (e.g. in ng/ml). Alternatively, normalization may occur with reference to a normalizing polypeptide which is known to be present in the sample in rather stable amounts.

In the methods of the invention, a sample obtained from a patient suffering from pancreatic cancer is examined for expression levels of PlGF and sFlt1. Expression levels of PlGF and sFlt1 in the sample can be analyzed by a number of methodologies, many of which are known in the art and understood by the skilled artisan, including but not limited to, immunohistochemical and/or Western blot analysis, immunoprecipitation, molecular binding assays, ELISA, ELIFA, fluorescence activated cell sorting (FACS) and the like, quantitative blood based assays (as for example Serum ELISA) (to examine, for example, levels of protein expression), biochemical enzymatic activity assays, in situ hybridization, Northern analysis and/or PCR analysis of mRNAs, as well as any one of the wide variety of assays that can be performed by gene and/or tissue array analysis.

Preferably, in the method of the invention expression levels of PlGF and sFlt1 are determined on the basis of mRNA, cDNA or polypeptide, more preferably on the basis of polypeptide.

In the method of the invention, a ratio is calculated between the individual expression levels of PlGF and sFlt1 in the sample of the pancreatic cancer patient. This ratio can be determined using a particular metric, wherein by "metric" is meant a measure. The metric to be used is that which best discriminates between expression levels of PlGF and sFlt1 in a pancreatic cancer patient having neural invasion and a normal control subject. It should be noted that in the ratio used in the method of the invention other factors or expression levels of other polypeptides or genes may be considered in addition to the expression levels of PlGF and sFlt1. In a suitable metric for calculation of the ratio of the method of the invention, the expression level of PlGF can be used in the numerator. In this case, the expression level of sFlt1 is used in the denominator. Alternatively, the expression level of PlGF can be used in the denominator. In this case, the expression level of sFlt1 is used in the numerator.

Preferably, the ratio of expression levels of PlGF and sFlt1 is calculated using the metric [PlGF/sFlt1], wherein the ratio is expressed using the expression level of PlGF in the numerator. Alternatively, the ratio of expression levels of PlGF and sFlt1 is calculated using the metric [sFlt1/PlGF], wherein the ratio is expressed using the expression level of PlGF in the denominator. It is to be understood that with regard to the successful use of the method the reciprocal metric [sFlt1/PlGF] is equivalent to the metric [PlGF/sFlt1] with the proviso that each ratio expressed by the metric [sFlt1/PlGF] will be compared to the respective reciprocal threshold values expressly disclosed herein for use with the metric [PlGF/sFlt1] and with the proviso that a decrease in the ratio [sFlt1/PlGF] will be informative instead of an increase as for the ratio [PlGF/sFlt1]. Depending on the metric that is used, the diagnostic indicator of neural invasion may be significantly above or below a ratio of a reference sample or a predetermined threshold value.

In the method of the invention, a deviation in the ratio of the expression levels of PlGF and sFlt1 can be the result of a decrease in the level of sFlt1. Alternatively or in addition, the deviation in ratio can be based on an increase in the level of PlGF.

In the method of the invention, sFlt1 expression level is measured by measuring the amount of free, bound (i.e., bound to growth factor), or total sFlt-1 (bound+free). Preferably, the expression level of sFlt1 refers to total sFlt1. PlGF expression levels are determined by measuring the amount of free PlGF (i.e., not bound to sFlt1 or another receptor) or total PlGF. Preferably, the expression level of PlGF is determined on basis of total PlGF.

The term "sample" as used herein, refers to a composition or biological probe that is obtained or derived from a subject of interest, preferably a pancreatic cancer patient, that contains a cellular and/or other molecular entity that is to be characterized and/or identified, for example based on physical, biochemical, chemical and/or physiological characteristics. In one embodiment, the definition encompasses blood and other liquid samples of biological origin like e.g. body fluids, and tissue samples such as a biopsy specimen or tissue cultures or cells derived therefrom. The source of the tissue sample may be solid tissue as from a fresh, frozen and/or preserved organ or tissue sample or biopsy or aspirate; blood or any blood constituents; bodily fluids; and cells from any time in gestation or development of the subject or plasma. Samples may be obtained from a pancreatic cancer patient prior to commencement of treatment (e.g., cancer treatment) or after commencement of treatment (e.g., cancer treatment).

The term "sample" includes biological samples that have been manipulated in any way after their procurement, such as by treatment with reagents, solubilization, or enrichment for certain components, such as proteins or polynucleotides, or embedding in a semi-solid or solid matrix for sectioning purposes. For the purposes herein a "section" of a tissue sample is meant a single part or piece of a tissue sample, e.g. a thin slice of tissue or cells cut from a tissue sample.

Samples include, but not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof. Preferably, the sample comprises or is derived from serum, plasma and/or urine.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood.

In the method of the invention, the ratio of the expression levels of PlGF and sFlt1 in a sample of a pancreatic cancer patient is compared to the respective ratio of a reference sample or a predetermined threshold value.

A "reference sample," as used herein, refers to any sample, standard, or level that is used for comparison purposes. In one embodiment, a reference sample is obtained from a healthy and/or non-diseased part of the body (e.g., tissue or cells) of the same subject or patient. In another embodiment, a reference sample is obtained from an untreated tissue and/or cell of the body of the same subject or patient. In yet another embodiment, a reference sample is obtained from a healthy and/or non-diseased part of the body (e.g., tissues or cells) of an individual who is not the subject or patient. In even another embodiment, a reference sample is obtained from an untreated tissue and/or cell part of the body of an individual who is not the subject or patient.

In certain embodiments, a reference sample is a single sample or combined multiple samples from the same subject or patient that are obtained at one or more different time points than when the test sample is obtained. For example, a reference sample is obtained at an earlier time point from the same subject or patient than when the test sample is obtained. Such reference sample may be useful if the reference sample is obtained during initial diagnosis of cancer and the test sample is later obtained when the cancer becomes metastatic.

In certain embodiments, a reference sample includes all types of biological samples as defined above under the term "sample" that is obtained from one or more individuals who is not the subject or patient. In certain embodiments, a reference sample is obtained from one or more individuals who are not the subject or patient to be tested.

In certain embodiments, a reference sample is a combined multiple samples from one or more healthy individuals who are not the subject or patient. In certain embodiments, a reference sample is pooled RNA samples from normal tissues or pooled plasma or serum samples from one or more individuals who are not the subject or patient. In certain embodiments, a reference sample is pooled RNA samples from tumor tissues or pooled plasma or serum samples from one or more individuals with a disease or disorder (e.g., pancreatic cancer) who are not the subject or patient.

Preferably, the reference sample is obtained from one or more subjects not suffering from pancreatic cancer like e.g. from healthy donors.

In the method according to the invention, the ratio of the expression levels of PlGF and sFlt1 of the patient sample is compared to a predetermined threshold value.

It has surprisingly been found that, when the ratio is expressed using the expression level of PlGF in the numerator, a suitable predetermined threshold value which is selected from the range of 0.15 to 0.35, preferably from the range of 0.2 to 0.3, more preferably from the range of 0.22 to 0.26, is particularly informative and allows for a meaningful discrimination between patients which do suffer from neural invasion and patients which do not. In particular, when the ratio is expressed using the expression level of PlGF in the numerator, a ratio of expression levels of PlGF and sFlt1 which exceeds a threshold value of about 0.22, preferably of about 0.23, more preferably of about 0.24 or 0.25, is informative for the presence of neural invasion, disease prognosis and patient stratification. It has been found that, when the ratio is expressed using the expression level of PlGF in the numerator, the higher the actual ratio of expression levels of PlGF and sFlt1 of a particular patient is above the threshold value, the more extensive is the neural invasion, and the less favourable is the disease prognosis for this patient.

It should be noted that, when the ratio of expression levels of PlGF and sFlt1 in a sample of a pancreatic cancer patient is expressed using the expression level of PlGF in the denominator, the reciprocal of the threshold values mentioned above is to be used and the ratio is informative if the ratio is decreasing said reciprocal threshold value. In other words, it has surprisingly been found that, when the ratio is expressed using the expression level of PlGF in the denominator, a suitable predetermined threshold value which is selected from the range of 6.67 to 2.86, preferably from the range of 5 to 3.33, more preferably from the range of 4.55 to 3.85, is particularly informative and allows for a meaningful discrimination between patients which do suffer from neural invasion and patients which do not. In particular, when the ratio is expressed using the expression level of PlGF in the denominator, a ratio of expression levels of PlGF and sFlt1 which falls below a threshold value of about 4.55, preferably of about 4.35, more preferably of about 4.17 or 4, is informative for the presence of neural invasion, disease prognosis and patient stratification. It has been found that, when the ratio is expressed using the expression level of PlGF in the denominator, the lower the actual ratio of expression levels of PlGF and sFlt1 of a particular patient is below the threshold value, the more extensive is the neural invasion, and the less favourable is the disease prognosis for this patient.

The present invention also refers to a kit for performing a method for identifying neural invasion in a pancreatic cancer patient according to the invention, the kit comprising means for determining the expression level of PlGF and/or sFlt1 as well as instructions for using said kit to calculate a relationship between the expression levels of PlGF and sFlt1.

The kits of the invention have a number of embodiments. A typical embodiment is a kit comprising a container, a label on said container, and a composition contained within said container; wherein the composition includes a primary antibodies that bind to PlGF and sFlt1, the label on the container indicating that the composition can be used to evaluate the presence of PlGF and sFlt1 in a sample, and instructions for using the antibody for evaluating the expression levels of PlGF and sFlt1 in a sample. Further, the kit comprises instructions for using said kit to calculate a relationship between the expression levels of PlGF and sFlt1. The kit can further comprise a set of instructions and materials for preparing a tissue, cell or body fluid sample. The kit may include both a primary and secondary antibody, wherein the secondary antibody is conjugated to a label, e.g., an enzymatic label.

Another embodiment is a kit comprising a container, a label on said container, and a composition contained within said container; wherein the composition includes one or more polynucleotides that hybridize to PlGF and sFLT1 under stringent conditions, the label on said container indicates that the composition can be used to evaluate the presence of PlGF in at least one type of sample, and instructions for using the polynucleotides for evaluating the presence of PlGF and sFLT1 mRNA or cDNA in at least one type of sample. Further, the kit comprises instructions for using said kit to calculate a relationship between the expression levels of PlGF and sFLT1. The kit can further comprise a set of instructions and materials for preparing a tissue, cell or body fluid sample.

Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

The present invention is also directed to a use of the method of the invention for assigning a pancreatic cancer patient to a specific therapy, preferably the specific therapy is selected from partial or full tumour resection, neoadjuvant chemo- and/or radiation-therapy, adjuvant chemo- and/or radiation-therapy and/or palliative therapy including palliative pain therapy. In the use of the method of the invention for disease prognosis, preferably the higher the ratio between expression levels of PlGF and sFlt1, when the ratio is expressed using the expression level of PlGF in the numerator, for the pancreatic cancer patient is above the reference sample or threshold value, the less favourable the disease prognosis is for this patient.

In the following, specific examples of such stratification to specific treatment schemes are described in more detail:

Circulating PlGF and sFlt1 are easily accessible biomarkers which can be repeatedly quantified in the serum of PDAC patients in routine laboratory tests. Since circulating PlGF and sFlt1 levels in the serum of PDAC patients correlate with NI in pancreatic cancer, a ratio thereof according to the invention can be applied in the clinical management of PDAC patients as follows:

Using PlGF and sFlt1 as Circulating Serum Biomarkers to Predict the Probability of NI and to Stratify Patients to Prognostic Subgroups As shown herein, the ratio of circulating levels of PlGF and sFlt1 correlates to NI in patients with PDAC. Determining PlGF and sFlt1 circulating serum levels prior to treatment, thus, allows stratifying patients to prognostic subgroups. Accordingly, PDAC patients with high levels of PlGF/sFlt1 (i.e. a ratio exceeding a predetermined threshold value) are allocated to the subgroup of patients with high risk of NI and consequently high risk of local tumor recurrence, reduced disease-free survival (DFS), overall survival, and poor prognosis.

Using PlGF and sFlt1 as Circulating Serum Biomarkers to Allocate Patients to Neoadjuvant Therapeutic Regimens Neoadjuvant therapeutic regimens can reduce NI in PDAC. Determining a ratio of circulating PlGF and sFlt1 in the serum prior to treatment will allow identifying those patients with high risk of NI, who will benefit from neoadjuvant therapy by reducing NI upfront to surgery. These findings translate into the clinical management of patients as follows: According to current guidelines, patients with small respectable tumors usually receive upfront surgery. However, if these patients are diagnosed with high PlGF/sFlt1 serum ratio at time of diagnosis, they will have a high risk of early tumor recurrence and reduced disease-free survival (DFS) due to NI and hence likely benefit from upfront neoadjuvant therapy to reduce NI (see FIG. 12).

In patients who are not eligible to receive neoadjuvant or adjuvant chemotherapy due to comorbidities, determining a ratio of circulating PlGF and sFlt1 allows to identify the subgroup of patients who are unlikely to benefit from surgery when evaluating the trade-off between expected perioperative morbidity and mortality risks and the risk of early local tumor recurrence due to NI. Thus, a ratio of PlGF and sFlt1 represents a biomarker which allows deciding on the treatment options in PDAC patients in order to avoid vain surgery and thereby improve patient's quality of life (see FIG. 13).

Using a Ratio of Circulating PlGF and sFlt1 Serum Levels as Therapeutic Biomarkers to Stratify and Allocate Patients To Targeted Therapy with Anti-PlGF directed Treatments for Specific Inhibition of Neural Invasion It is an ongoing matter of debate to what extent neoadjuvant therapy reduces NI in pancreatic cancer. Some reports from clinical trials indicate a significant reduction in NI following neoadjuvant chemotherapy, while a recent report suggests that these effects may only be minor. The latter notion is in line with the clinical observation that neoadjuvant chemotherapy prolongs DFS primarily by increasing time to recurrence of distant metastasis while effects on local recurrence rate and time to local disease recurrence are minor. Thus, neoadjuvant chemotherapy impacts on the pattern of disease recurrence: it reduces recurrence rates of distant metastasis whilst local recurrence rates and time-to-local disease recurrence remain largely unchanged.

Indeed, treatment of neuronal cells with chemotherapy induces expression and secretion of PlGF by Schwann-cells, which ensheathe nerves. Since PlGF in turn supports survival and clonal growth of pancreatic cancer cells, even under conditions of chemotherapeutic treatment, the tumor-nerve interface may be considered as a microenvironmental niche within the tumor stroma, which protects tumor cells from chemotherapeutic treatment and therefore permits escape from chemotherapy and facilitates further metastatic spread of PDAC via tumor cell invasion along nerves (own unpublished work).

Blocking PlGF therefore constitutes a beneficial adjunct to chemotherapeutic treatment modalities by preventing PlGF-mediated escape from chemotherapy and thus blocking PlGF-mediated cell survival and tumor cell spread within the tumor cell-neural niche. This therapeutic strategy can be applied to the adjuvant chemotherapeutic setting following curative-intent surgery, but in particular has several potential benefits in the clinical setting of neoadjuvant chemotherapy in PDAC patients. Indeed, given that neoadjuvant chemotherapy might only have limited efficacy on reducing neural invasion, a potential clinical drawback for neoadjuvant therapy is the risk of progression of NI while waiting for surgery, thus limiting the success of curative-intent surgery.

Figure 12:
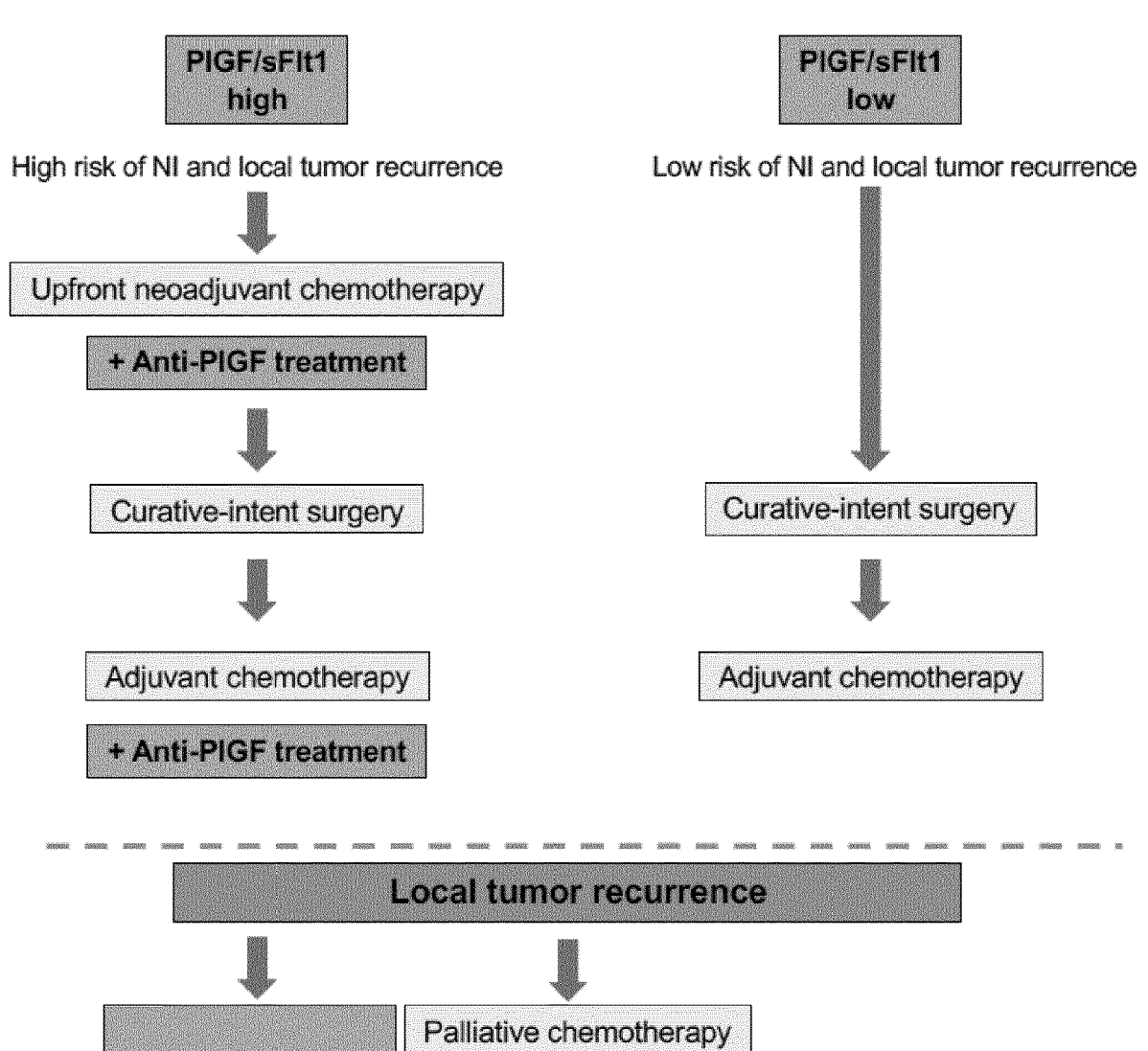

Blocking PlGF using targeted anti-PlGF treatment modalities in adjunct to neoadjuvant chemotherapy hence addresses the following aims:

In patients with upfront resectable tumors but elevated circulating PlGF/sFlt1 ratios and consequently high risk of extended NI and early local tumor recurrence (i.e. reduced DFS), anti-PlGF directed treatments given in adjunct to neoadjuvant chemotherapy would (i) prevent PlGF-mediated escape from chemotherapy, (ii) increase efficacy of neoadjuvant chemotherapy and (iii) thereby reduce NI within the tumor cell-neural niche, (vi) ultimately resulting in lower local tumor recurrence rates and longer DFS (see FIG. 12).

In patients with borderline-resectable tumors, neoadjuvant chemotherapy to shrink tumor size is mandatory if curative-intent surgery is an option. Therefore, blocking PlGF using anti-PlGF directed treatments in adjunct to neoadjuvant chemotherapy in patients with high circulating PlGF/sFlt1 ratios has the potential benefit to reduce neural invasion in addition to tumor mass shrinkage and hence lower local tumor recurrence rates following curative-intent surgery (see FIG. 14).

Moreover, while waiting for surgery, circulating PlGF and sFlt1 can repeatedly be quantified in serum of patients with borderline-resectable PDAC, in whom initial PlGF/sFlt1 levels were not elevated prior to start of chemotherapy. If circulating PlGF/sFlt1 serum ratios increase, anti-PlGF directed treatment can be initiated in order to prevent progression of neural invasion (see FIG. 14).

In the adjuvant setting, anti-PlGF directed treatment modalities address the following aims:

Following curative-intent surgery, allocation of patients to anti-PlGF directed treatment can be based on the determination of circulating PlGF and sFlt1 levels prior to surgery, or prior to neoadjuvant therapy, respectively. Accordingly, in patients with histologic proof of neural invasion of extratumoral nerves, who are eligible for adjuvant chemotherapy following curative-intent surgery and who initially presented with elevated circulating PlGF/sFlt1 ratios prior to surgery, anti-PlGF directed treatments can be given in adjunct to adjuvant chemotherapy in order to increase the efficacy of adjuvant chemotherapy within the tumor cell-neural niche, reduce local tumor recurrence rate and increase DFS (see FIGS. 12 and 14).

Figure 14:
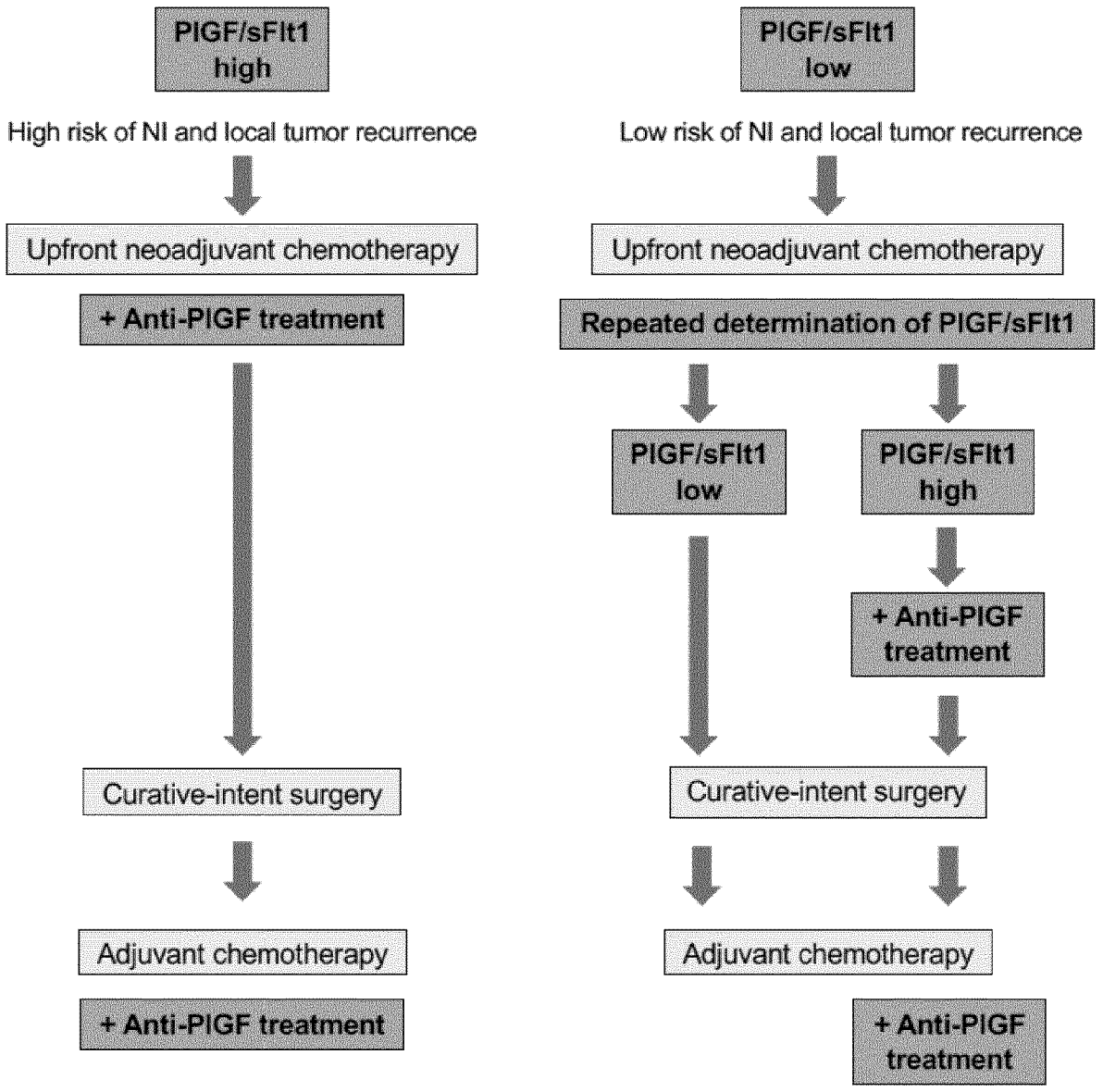

Finally, if patients are not eligible for adjuvant chemotherapy e.g. due to reduced clinical performance status or co-morbidities which preclude from chemotherapy, anti-PlGF directed treatments can be given as monotherapy to block PlGF-mediated tumor cell growth and invasion along nerves (see FIGS. 12 and 14).

Using a Ratio of Circulating PlGF and sFlt1 Serum Levels as Therapeutic Biomarkers to Stratify and Allocate Patients to Targeted Therapy With Anti-PlGF Directed Treatments for Specific Inhibition of Neuropathic Pain in the Palliative Setting NI constitutes a major cause of neuropathic pain, which often is difficult to treat, thus limiting the quality of life. Data presented herein correlates circulating PlGF/sFlt1 serum ratios with perceived neuropathic pain in PDAC patients with unresectable advanced or metastatic PDAC (representing palliative disease) and more specifically characterize a functional role of PlGF in cancer related structural remodelling of neural plasticity. Thus, blocking PlGF by anti-PlGF antibodies abrogated cancer mediated neurite outgrowth from primary DRG neurons in ex vivo co-culture models, and hence reduced neural remodelling and plasticity. Moreover, tumor PlGF mRNA transcript levels correlate with nerve area in PDAC tissues.

Thus, in the palliative setting, anti-PlGF directed treatment modalities represent a useful therapeutic tool in order to treat neuropathic pain and alleviate quality of life in patients with unresectable tumors or local tumor recurrence either in conjunct with palliative chemotherapy or given as monotherapy. Determining a ratio of circulating PlGF and sFtl1 will allow identifying those patients who likely benefit form anti-PlGF directed treatment of neuropathic pain (see FIGS. 12-14).

Further, the present invention is also directed to a method of predicting responsiveness of a pancreatic cancer patient to an anti-PlGF therapy, said method comprising the steps of a method for identifying neural invasion in a pancreatic cancer patient according to the invention, wherein, when the ratio is expressed using the expression level of PlGF in the numerator, an increase in the ratio between expression levels of PlGF and sFlt1 above the reference sample or threshold value is indicative of an increase in likeliness that this patient will benefit from anti-PlGF therapy.

The present invention is also directed to a method of predicting whether a pancreatic cancer patient will benefit from partial or full tumour resection, the method comprising the steps of a method for identifying neural invasion in a pancreatic cancer patient according to the invention, wherein, when the ratio is expressed using the expression level of PlGF in the numerator, the higher the ratio between expression levels of PlGF and sFlt1 for the pancreatic cancer patient is above the reference sample or threshold value, the less likely this patient will benefit from partial or full tumour resection.

The term "diagnosis" is used herein to refer to the identification of a molecular or pathological state, disease or condition, such as the identification of cancer or to refer to identification of a cancer patient who may benefit from a particular treatment regimen.

The term "prognosis" is used herein to refer to the prediction of the likelihood of clinical benefit from anti-cancer therapy.

The term "prediction" is used herein to refer to the likelihood that a patient will respond either favourably or unfavourably to a particular anti-cancer therapy. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favourably to a treatment regimen, such as a given therapeutic regimen, including for example, administration of a given therapeutic agent or combination, surgical intervention, steroid treatment, etc., or whether long-term survival of the patient, following a therapeutic regimen is likely.

"Patient response" can be assessed using any endpoint indicating a benefit to the patient, including, without limitation, (1) inhibition, to some extent, of disease progression, including slowing down and complete arrest; (2) reduction in lesion size; (3) inhibition (i.e., reduction, slowing down or complete stopping) of disease cell infiltration into adjacent peripheral organs and/or tissues; (4) inhibition (i.e. reduction, slowing down or complete stopping) of disease spread; (5) relief, to some extent, of one or more symptoms associated with the disorder; (6) increase in the length of disease-free presentation following treatment; and/or (8) decreased mortality at a given point of time following treatment.

The term "long-term survival" is used herein to refer to survival for at least 1 year, 5 years, 8 years, or 10 years following therapeutic treatment.

The term "benefit" is used in the broadest sense and refers to any desirable effect and specifically includes clinical benefit as defined herein.

Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

To "reduce or inhibit" is to decrease or reduce an activity, function, and/or amount as compared to a reference. By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, the size or number of the blood vessels, or the extent of neural invasion.

In a further aspect, the present invention is directed to an anti-PlGF compound for use in the treatment of a pancreatic cancer patient suffering from neural invasion of the pancreatic tumor, wherein, when the ratio is expressed using the expression level of PlGF in the numerator, said pancreatic cancer patient has an increase in the ratio between the expression levels of PlGF and sFlt1 relative to a reference sample or a predetermined threshold value, preferably the pancreas cancer patient has a ratio between the expression levels of PlGF and sFlt1 above a threshold value of 0.22, more preferably of 0.23, even more preferably of 0.24 or 0.25.

By "compound" is meant any small molecule chemical compound, antibody, nucleic acid molecule, or polypeptide, or fragments thereof.

The term "anti-PlGF compound" as used herein refers to any type of compound which interferes directly with expression or activity of PlGF polypeptide, wherein expression levels and/or activity of PlGF peptide is inhibited or diminished.

The anti-PlGF compound for use according to the invention may be used alone, in combination with one or more pharmaceutically acceptable excipients and/or in combination with other active ingredients or therapeutic measures like e.g. cytotoxic or chemotherapeutic agents or radiotherapy.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer, preferably of pancreatic cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1l and calicheamicin omegal1; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2- ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Illinois), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g, erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine ana-log); antisense oligonucleotides, particularly those which inhibit expression of genes in signaling pathways implicated in aberrant cell proliferation, such as, for example, PKC-alpha, Raf and H-Ras; ribozymes such as a VEGF expres-sion inhibitor (e.g., ANGIOZYME® ribozyme) and a HER2 expression inhibitor; vaccines such as gene therapy vac-cines, for example, ALLOVECTIN® vaccine, LEUVEC-TIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

By "radio-therapy" or "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The anti-PlGF compound for use according to the inven-tion preferably comprises or consists of an anti-PlGF anti-body, preferably an anti-PlGF antibody which binds specifi-cally to PlGF, in particular to human PlGF.

In a preferred embodiment, the anti-PlGF antibody for use according to the invention is a blocking antibody. A "block-ing" antibody or an antibody "antagonist" is one which inhibits or reduces biological activity of the antigen it binds. For example, a PlGF-specific blocking antibody binds PlGF and inhibits the ability of PlGF to bind to one or all types of PlGF receptors in a patient or subject. Preferred blocking antibodies or antagonist antibodies completely inhibit the biological activity of the antigen.

The anti-PlGF antibody for use according to the invention preferably comprises the CDR regions corresponding to the sequences of CDR1 heavy chain with SEQ ID NO: 1 (GYTFTDYY), CDR2 heavy chain with SEQ ID NO: 2 (IYPGSGNT); CDR3 heavy chain with SEQ ID NO: 3 (VRDSPFFDY), CDR1 light chain with SEQ ID NO: 4 (QSLLNSGMRKSF), CDR2 light chain with SEQ ID NO: 5 (WAS) and CDR3 light chain with SEQ ID NO: 6 (KQSYHLFT). Said anti-PlGF antibody for use according to the invention can be provided in the form of a molecule selected from the group of Fab, Fab' or F(ab')2, a combina-tion of at least two complementarity determining regions (CDRs), a soluble or membrane-anchored single-chain vari-able part, or single variable domain.

Preferably, the anti-PlGF antibody for use according to the invention is characterized in that it comprises a heavy chain variable region comprising the sequence of SEQ ID NO: 7 and in that it comprises a light chain variable region comprising the sequence of SEQ ID NO. 8.

The anti-PlGF antibody for use according to the invention preferably is antibody 16D3 as produced by the cell line deposited as LMBP 6399CB or a fragment thereof.

The anti-PlGF antibody for use according to the invention preferably comprises or consists of the amino acid sequence of SEQ ID NO: 9 and/or the amino acid sequence of SEQ ID NO: 10.

The anti-PlGF antibody for use according to the invention is preferably selected from the group of Fab, Fab', F(ab')2, a single chain variable fragment or combinations thereof.

In a particularly preferred embodiment, the anti-PlGF antibody for use according to the invention is an antibody as described in EP 1 869 085 B1 and/or as defined in the claims of EP 1 869 085 B1, specifically in claims 1 to 8 of EP 1 869 085 B1.

The term "antibody" is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

The term "antibody fragment" refers to a sub-part of an antibody molecule which alone, or in combination with other fragments, is capable of binding to the antigen against which the corresponding antibody was raised. Typical anti-body fragments are Fab, Fab', F(ab')2, Fv or scFv, which often retain an affinity for the antigen which is comparable to the complete antibody. Smaller fragments include complementarity determining regions or CDRs such as CDR1, CDR2 and CDR3 of the heavy or light chain and/or combinations of two or more thereof.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collec-tively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the anti-body as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homolo-gous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biologi-cal activity.

"Humanized" forms of non-human (e.g., murine) anti-bodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies. Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. Alternatively, the human antibody may be prepared via immortalization of human B lymphocytes producing an antibody directed against a target antigen (such B lymphocytes may be recovered from an individual or may have been immunized in vitro).

In the following, the invention will be explained in more detail by way of examples.

FIGURES

FIG. 1: High circulating PlGF/sFlt1 serum ratio is associated with neural invasion and reduced survival in patients with PDAC following curative surgery. A, Elevated circulating PlGF/sFlt1 serum ratio (referred to as PlGF/sFlt1$^{circ}$) in the overall cohort of PDAC patients (n=80) as compared to healthy controls (ctr; n=80). Shown is the scatter dot plot with the median and interquartile range, p<0.0001, Mann-Whitney test. B, PlGF/sFlt1$^{circ}$ serum ratios do not differ between the subgroup of patients with non-resectable, i.e. locally advanced or metastatic tumors (M1, palliative, n=45) and the subgroup of patients with resectable tumors prior to curative-intent surgery (R0; n=35). Shown is the scatter dot plot with the median and interquartile range, p=0.869, Mann-Whitney test. C, Median PlGF/sFlt1$^{circ}$ serum ratios are elevated to 0.32 in patients with neural invasion (Pn1; n=25) as compared to 0.19 in patients without neural invasion (Pn0; n=20). Shown is the scatter dot plot with the median and interquartile range; p<0.0001, Mann-Whitney test. D, In contrast to neural invasion, PlGF/sFlt1$^{circ}$ serum ratios are not associated with the incidence of lymph node metastasis, which is in line with the notion that PlGF specifically functions as modifier at the tumor-nerve interface. Shown is the scatter dot plot with the median and interquartile range; n=11 for N0 (lymph node metastasis absent) and n=29 for N1 (lymph node metastasis present); p=0.55, Mann-Whitney test. E-F, Elevated PlGF/sFlt1$^{circ}$ serum ratios are associated with shorter overall survival in patients with PDAC who underwent curative-intent surgery (E), but not in patients with non-resectable (locally advanced or metastastic) PDAC undergoing palliative therapy (F). Shown is Kaplan-Meier survival in patients with PlGF/sFlt1$^{circ}$<median (n=15) or PlGF/sFlt1$^{circ}$>median (n=16), respectively, undergoing curative-intent surgery for resectable PDAC (HR: 4.106; 95% confidence interval: 1.131 to 14.91; Log-rank p=0.0128; E), and Kaplan-Meier survival in patients with palliative (non-resectable) disease allocated to groups with PlGF/sFlt1$^{circ}$<median (n=18) and PlGF/sFlt1$^{circ}$>median (n=19); HR: 0.845; 95% confidence interval: 0.3264 to 2.187; Log-rank p=0.153 (H). G, Elevated PlGF/sFlt1$^{circ}$ is associated with the severity of tumor-related pain. Pain was quantified using visual analogue scales (VAS 0-10) and grouped into mild (VAS 1-3), moderate (VAS 4-6), and strong pain (VAS 7-10). Shown are means±SEM of PlGF/sFlt1$^{circ}$ serum ratios in patients allocated to groups with mild, moderate or strong pain, respectively (*p<0.01; Mann-Whitney test).

Figure 2:
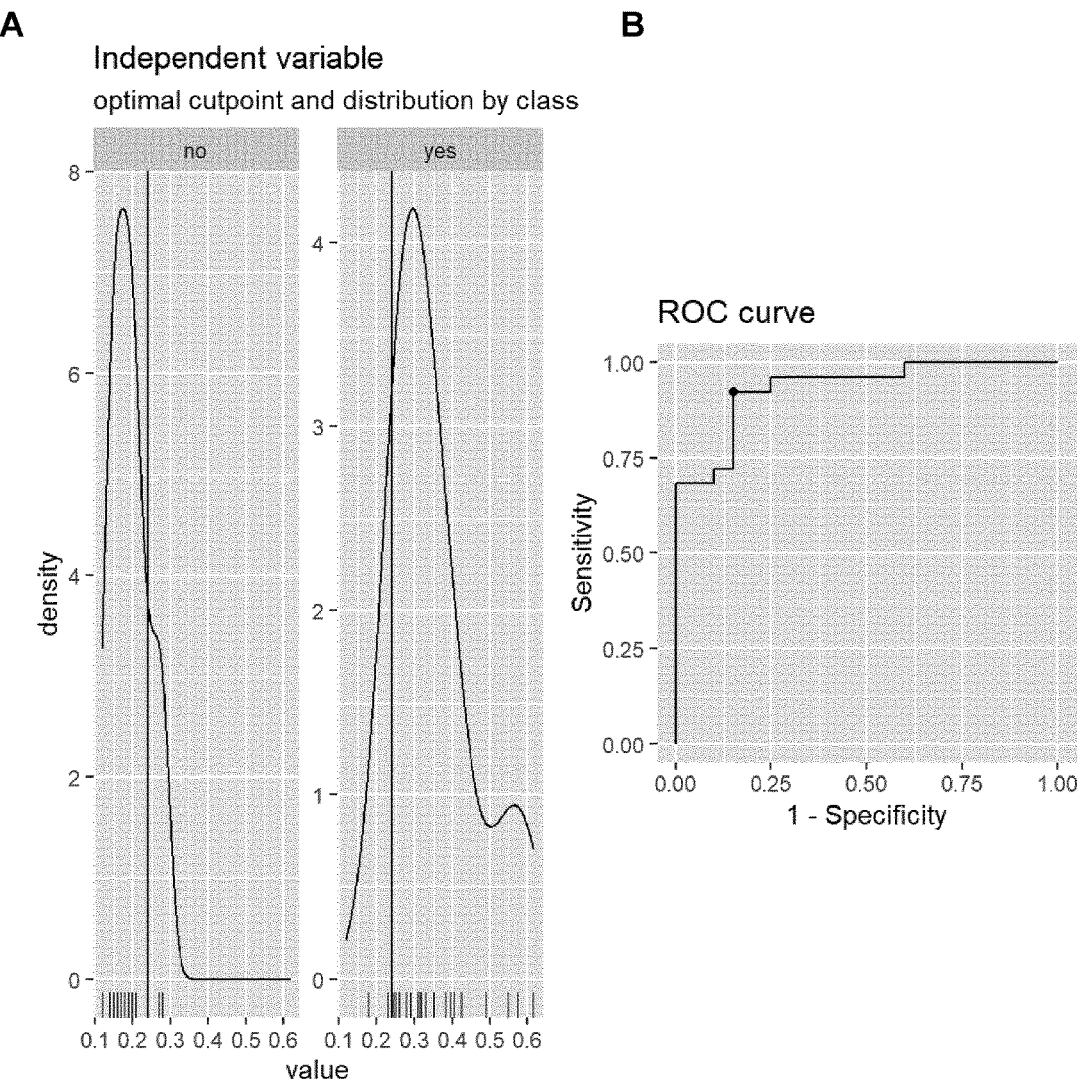

FIG. 2: Optimal cut point and ROC curve analyses of PlGF/sFlt1$^{circ}$ serum ratios were performed using CRAN cutpointr software. A, Panel depicts optimal cut point and distribution of PlGF/sFlt1$^{circ}$ by class. Analysis displayed 92.0% sensitivity and 85.0% specificity for the discrimination between patients without neural invasion (no) and patients with neural invasion (yes) at a cut-off PlGF/sFlt1$^{circ}$ serum ratio of 0.2404 (95% confidence interval: 0.23-0.31). B, Panel depicts corresponding ROC curve of PlGF/sFlt1$^{circ}$ (AUC=0.935; 95% confidence interval: 0.855-0.992).

Figure 3:
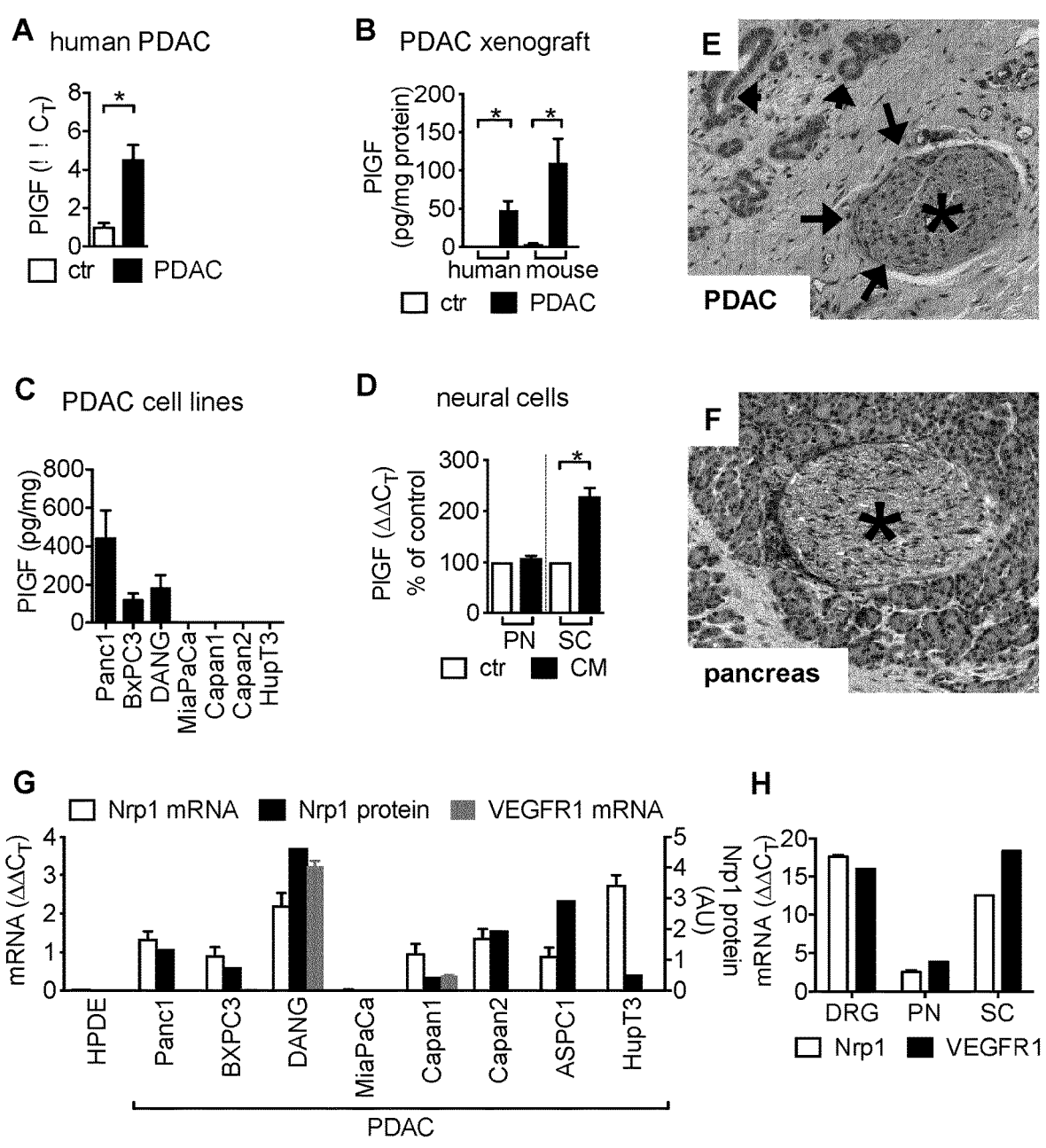

FIG. 3: PlGF and its receptors are expressed at the tumor-nerve interface. A, PlGF mRNA expression in tissues of human PDAC (n=24) and corresponding healthy pancreas (control; ctr) was determined using qPCR and normalized to GAPDH. Shown is the bar graph with mean±SEM; p=0.002. (B) Human DANG pancreatic tumor cells were grown orthotopically in the pancreas of NMRI$^{nu/nu}$ mice, and human (representing tumor cell derived) and murine (representing host derived) PlGF proteins in orthotopic tumor (PDAC) and paired healthy pancreatic tissues (control; ctr) determined using species-specific ELISA. Host-derived murine PlGF (indicated as mouse) is rarely expressed in the pancreas of mice (control; ctr) but induced in the stroma of PDAC xenografts. Tumor cell derived PlGF (indicated as human) is expressed in xenografted tumors. *p<0.01. C, ELISA based quantification of PlGF protein in supernatants of various human PDAC cell line cultures (n=3). D, Primary neurons (PN) and Schwann cells (SC) were isolated from newborn rats and cultivated with control media (ctr) or conditioned media (CM) derived from MiaPaca tumor cell cultures. PlGF mRNA expression was determined using qPCR, normalized to GAPDH and shown as mean±SEM (n=3; p=0.0072). PlGF expression is induced in Schwann cells upon cultivation with tumor cell conditioned supernatants. E-F, Representative IHC for the PlGF receptor Nrp1 in tissues of PDAC (E) and healthy pancreas (F). Intrapancreatic (in F) and intratumoral (in E) nerves are depicted by asterisks. Arrows point to Nrp1 expression in ductal epithelial cancer cells (arrowheads) and nerves (arrows). G, Nrp1 mRNA and protein as well as VEGFR1 mRNA expression levels were determined in human PDAC cell lines and in an immortalized human pancreatic ductal epithelial cell line (HPDE) using qPCR and normalized to GAPDH or immunoblotting, respectively (n=3). H, Expression of Nrp1 and VEGFR1 mRNA transcripts in dorsal root ganglia (DRGs), primary neurons (PN) and Schwan cells (SC) was determined using qPCR, normalized to GAPDH and shown as mean±SEM.

Figure 4:
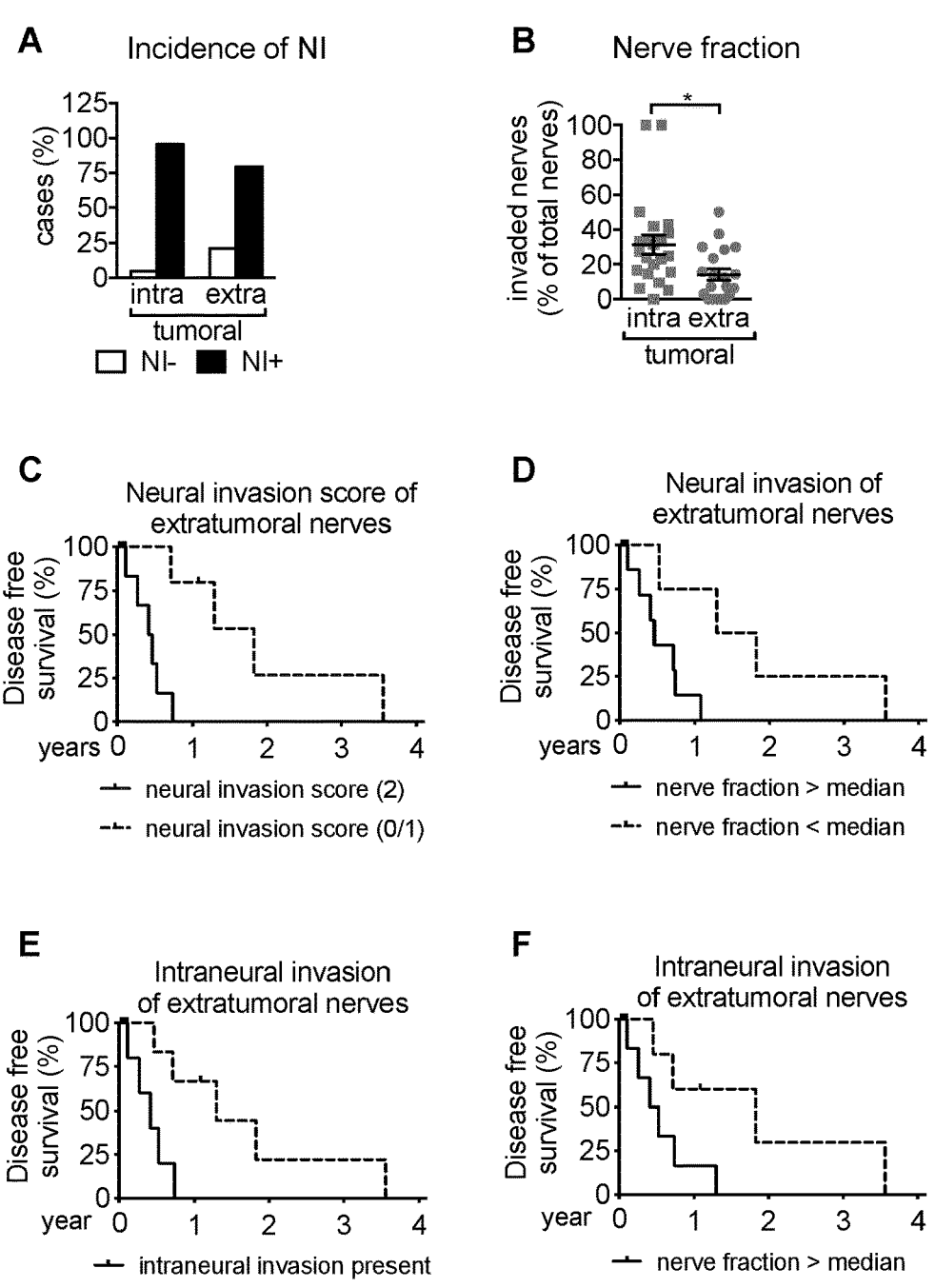

FIG. 4: The extent of neural invasion of extratumoral nerves predicts early disease recurrence. A-B, Morphometric analysis of neural invasion (NI) of nerves in PDAC specimens (referred to as intratumoral nerves) and in paired adjacent healthy pancreatic tissues (referred to as extratumoral nerves); n=24. Shown are (A) incidence of neural invasion in intra- and extratumoral nerves with absence (NI-) or presence (NI+) of neural invasion (p=0.19, Fisher's exact test) and (B) nerve fraction as determined by quantifying the percentage of tumor-invaded nerves per total nerves (p=0.002, Mann Whitney test). C-D, Within extratumoral nerves, a high neural invasion score (C) and a high nerve fraction (D; as determined by the fraction of tumor-invaded nerves per total nerves) are associated with shorter disease-free survival (DFS) in patients following curative-intent surgery. Shown is Kaplan-Meier disease-free survival in patients allocated to groups with extended invasion of extratumoral nerves (NI score 2) versus absent or focal neural invasion (NI score 0 and 1, respectively; HR: 4.46; 95% confidence interval: 1.069 to 18.60; Log-rank p=0.0042 in C), and in patients allocated to groups with extratumoral nerve fraction <median and nerve fraction >median (HR: 3.22; 95% confidence interval: 0.94 to 11.11; Log-rank p=0.0228 in D). E-F, Intraneural invasion (i.e. tumor cell invasion of the intraneural space) was quantified in extratumoral nerves (for a scheme displaying the respective morphometric analysis please refer to FIG. 6A). Kaplan-Meier depicts disease-free survival in the subgroups of patients with or without intraneural invasion of extratumoral nerves (HR: 3.63; 95% confidence interval: 0.90 to 14.70; Log-rank p=0.0037), and in patients allocated to groups with intraneural nerve fraction of extratumoral nerves<median and nerve fraction>median (HR: 3.78; 95% confidence interval: 0.82 to 17.38; Log-rank p=0.0139.

Figure 5:
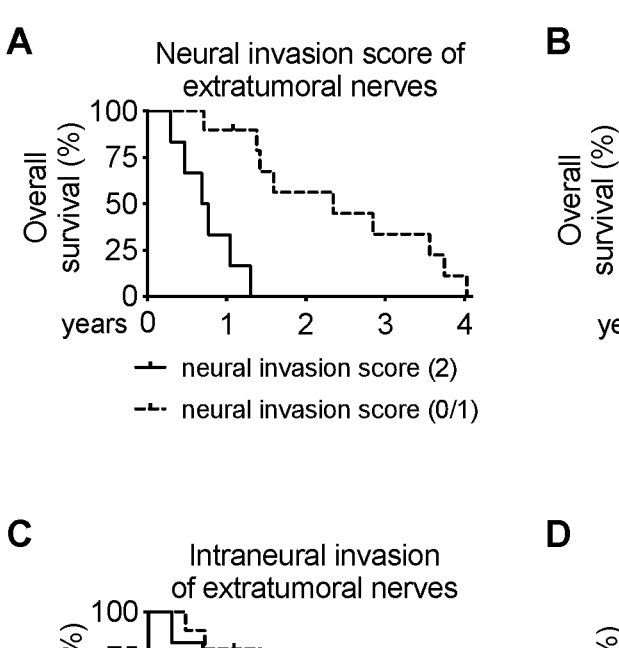
Figure 5:
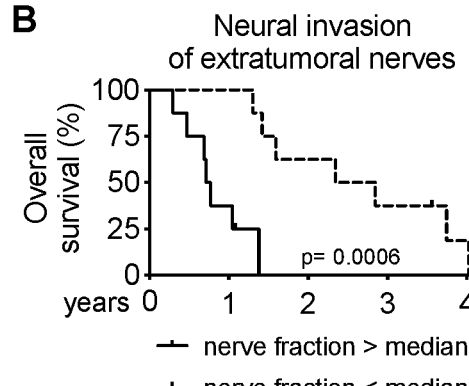
Figure 5:
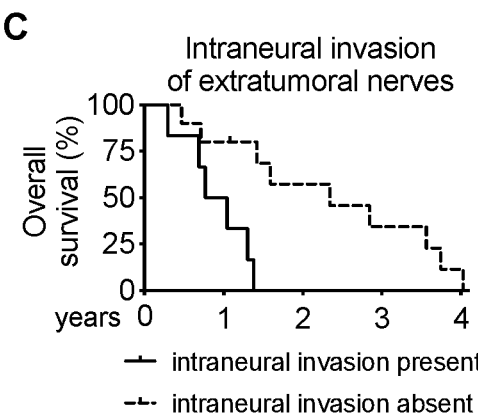
Figure 5:
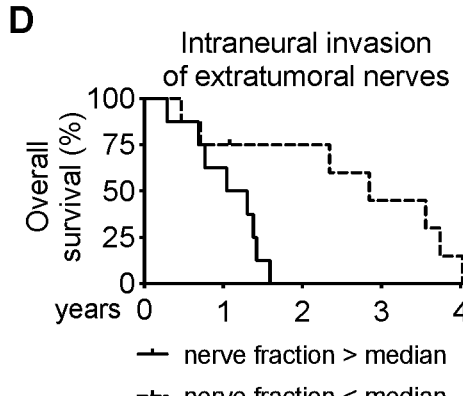

FIG. 5: The extent of neural invasion of extratumoral nerves is associated with reduced overall survival. A-B, Neural invasion was quantified in extratumoral nerves. Shown is Kaplan-Meier overall survival in patients allocated to groups with extended extratumoral NI (NI score 2) versus absent or focal NI (NI score 0 and 1, respectively; HR: 4.46; 95% confidence interval: 1.069 to 18.60; Log-rank p=0.0042 in A), and in patients allocated to groups with extratumoral nerve fraction <median and nerve fraction >median (HR: 3.22; 95% confidence interval: 0.94 to 11.11; Log-rank p=0.0228 in B). C-D, Intraneural invasion was quantified in extratumoral nerves. Kaplan-Meier depicts overall survival in the subgroups of patients with or without intraneural nerve invasion of extratumoral nerves (HR: 3.63; 95% confidence interval: 0.90 to 14.70; Log-rank p=0.0037), and in patients allocated to groups with intraneural nerve fraction of extratumoral nerves <median and nerve fraction >median (HR: 3.78; 95% confidence interval: 0.82 to 17.38; Log-rank p=0.0139.

Figure 6:
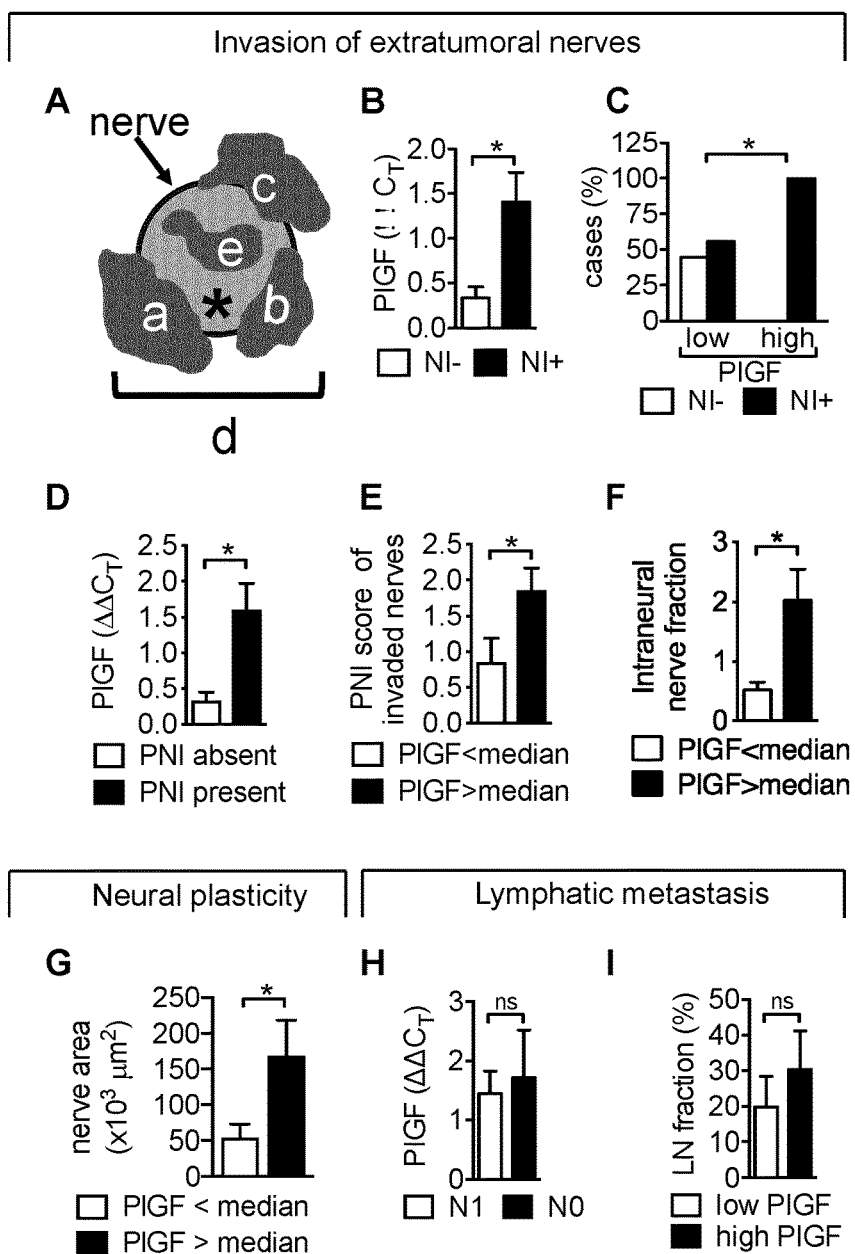

FIG. 6: Expression of PlGF mRNA transcripts correlates with the extent of neural invasion of extratumoral nerves and increased neural plasticity. A, Morphometric analysis of neural invasion of nerves in PDAC. Scheme illustrates invasion of a nerve (indicated by asterisk) by tumor cell colonies (a, b, c, and e). Morphometric analysis depicts tumor invasion of perineural sheath (referred to as perineural invasion; a-c), the circumferential range of perineural invasion (d=a+b+c) and the invasion of the intraneural nerve space (referred to as intraneural invasion; e) of nerves in tumor tissues (intratumoral) and adjacent healthy pancreas (extratumoral). B, PlGF mRNA transcript levels in tumors without (NI-) and with neural invasion (NI+) of extratumoral nerves are shown as means±SEM, n=24, p=0.0043, Mann-Whitney test. C, Incidence of extratumoral neural invasion in tumors with low (<median) or high (>median) PlGF mRNA transcript levels (n=24, p=0.0325; Fisher's exact test). D, PlGF mRNA transcript levels in tumors without (PNI absent) or with perineural invasion (PNI present) of extratumoral nerves shown as means±SEM (n=24, p=0.0139; Mann-Whitney test). E, Circumferential range of perineural invasion of extratumoral nerves was morphometrically determined and scored as 0 (absent), 1 (¼ circumference), 2 (½ circumference), 3 (¾ circumference), and 4 (whole circumference). Shown are PNI scores as means±SEM of affected extratumoral nerves in tumors allocated to groups with PlGF transcript levels <median or >median (n=24, p=0.0331; Mann-Whitney test). F, Intraneural nerve fraction is determined as the percentage of extratumoral nerves exhibiting intraneural tumor invasion per total nerves analyzed. Bar graph depicts intraneural nerve fraction as mean±SEM in tumors allocated to groups with PlGF transcript levels <median and >median (n=24, p=0.0133; Mann-Whitney test). G, Neural plasticity is increased in tumors with high PlGF mRNA expression levels. Nerve area was morphometrically determined in PDAC tissues and shown as mean±SEM in tumors allocated to groups with PlGF transcript levels <median or >median (n=24, p=0.046; unpaired t-test). H-I, In contrast to neural invasion and neural plasticity, PlGF mRNA expression does not correlate with lymphatic metastasis. PlGF mRNA transcript levels in tumors without (N0) and with lymphatic metastasis (N1). Shown are mean±SEM, n=24, p=0.55, Mann-Whitney test (H). Lymph node fraction as determined by the percentage of tumor-infiltrated lymph nodes per total lymph nodes analyzed (I; p=0.65; Mann-Whitney test) in tumors with low (<median) or high (>median) PlGF mRNA transcript levels.

Figure 7:
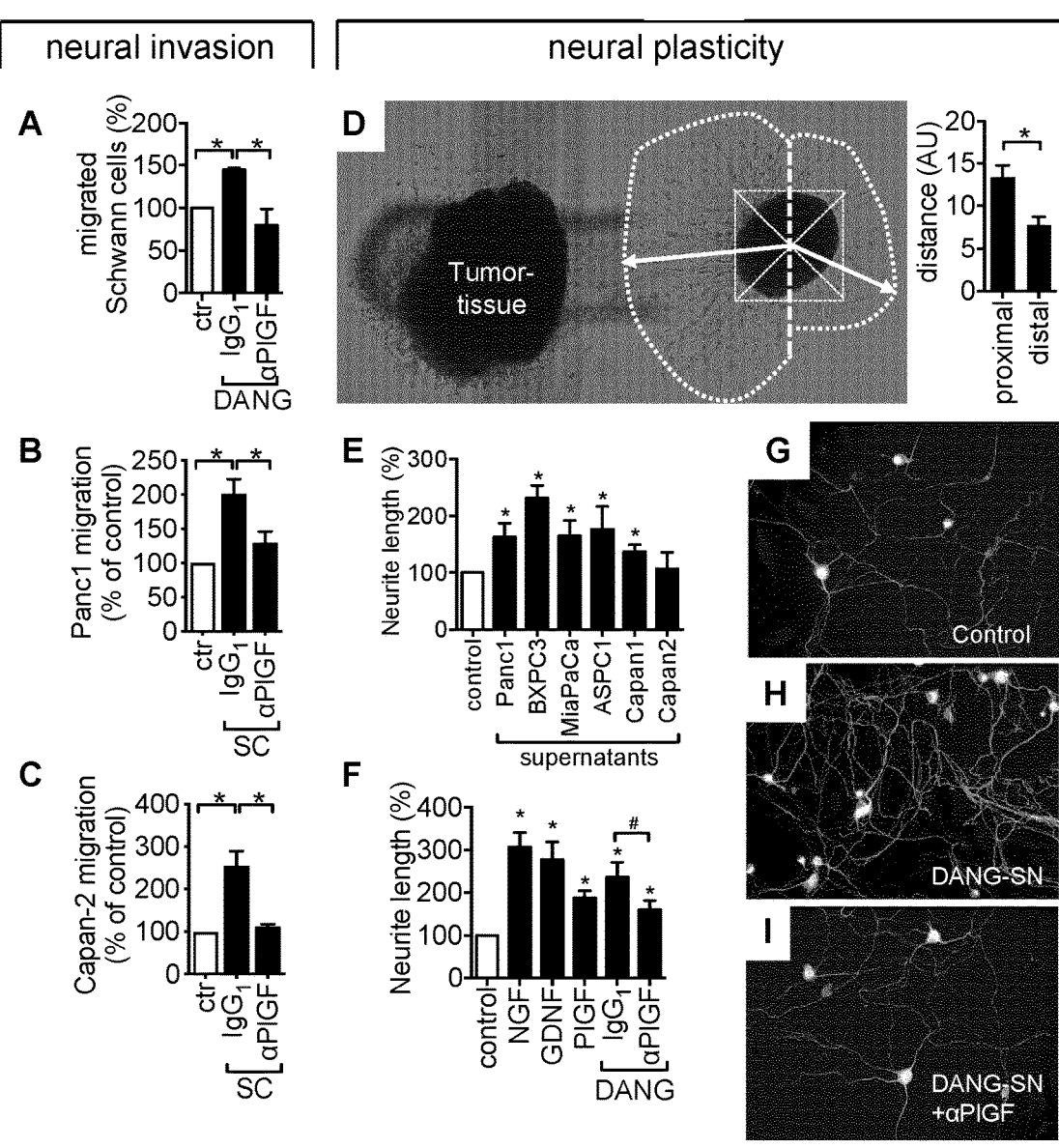

FIG. 7: PlGF mediates mutual chemoattraction between tumor cells and Schwann cells and stimulates neurite outgrowth. A, Schwann cells were seeded in the upper chamber of transwell inserts and allowed to migrate towards conditioned media from DANG cell monolayers (seeded in the lower chamber) or control media for 16 h. Neutralizing PlGF using anti-PlGF antibodies inhibits directed migration of Schwann cells as compared to $IgG_1$ control. Shown are means±SEM; n=5; p<0.0001, Mann-Whitney t-test. B-C, Anti-PlGF inhibits directed migration of Panc1 (B) and Capan-2 (C) cells towards chemoattractant stimuli from conditioned Schwann-cell supernatants placed in the lower chamber (n=3; p<0.05). D, DRGs were co-cultured in 3D-matrigel with explanted PDAC xenograft tumor tissue and neurite outgrowth monitored by in vivo phase contrast microscopy. Neurite outgrowth from DRGs towards gradients released by PDAC tissues was determined by measuring the radial distance of the longest neurite extensions from the center of the DRG (proximal); distal: extensions of outgrowing neurites at the opposite site of the DRG as control (n=8; p<0.001). E-I, Whole primary DRG cell cultures (containing neurons and Schwann cells) were isolated from newborn rat DRGs and incubated with supernatants from various PDAC cells (E) or medium containing recombinant nerve growth factor (NGF), glial-derived nerve growth factor (GDNF) and PlGF (F). Overall neurite length was determined (n=3-5, p<0.05) using NeuroQuant® software based on selective immunofluorescent staining of primary neurons for neuron-specific Tuj-1. PlGF stimulates neurite outgrowth. Anti-PlGF was used to neutralize PlGF secreted by DANG cells, resulting in marked inhibition of neurite outgrowth. Representative images of primary neurons cultured with control media (G), DANG supernatant (H) and DANG supernatant with anti-PlGF (I) following selective IF-staining for neuron-specific Tuj-1.

Figure 8:
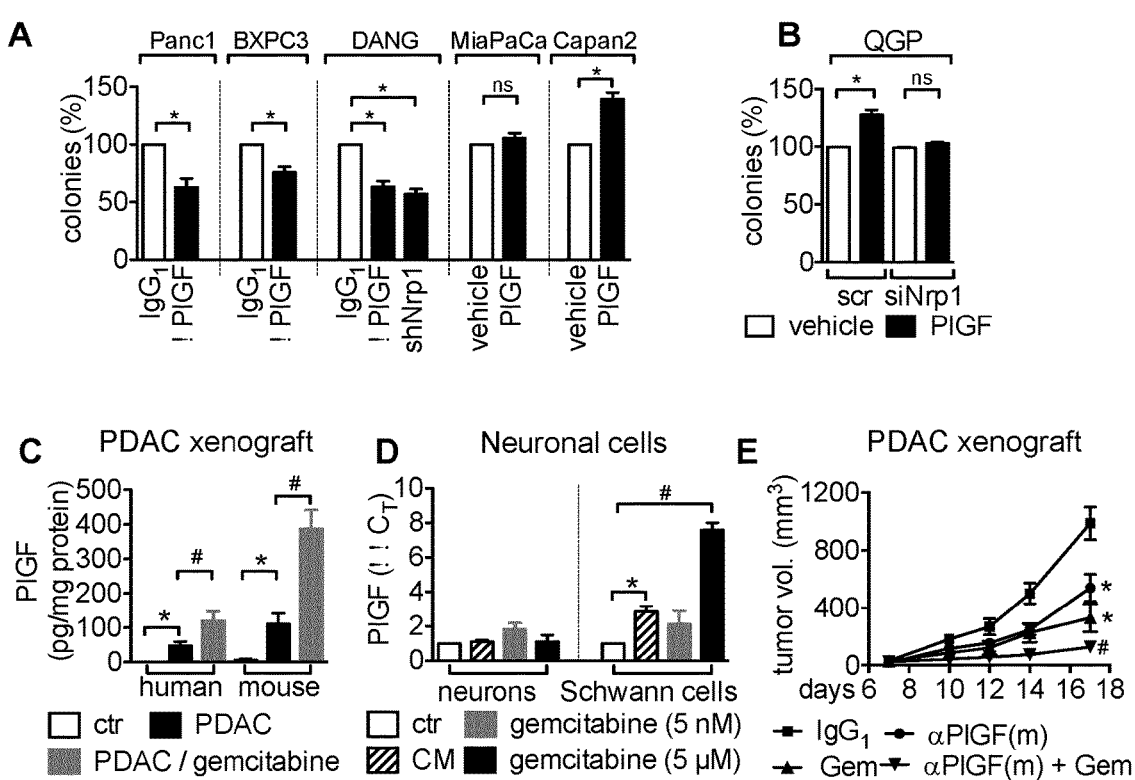

FIG. 8: PlGF stimulates clonal growth of PDAC cell lines via Nrp1. A-B, Human PDAC (A) and pancreatic neuroendocrine tumor cell lines (B) were subjected to HTCA assays and the effects of PlGF (100 ng/ml), anti-PlGF antibodies and Nrp1-receptor knock-down using shRNA on clonal growth determined (A). Loss of responsiveness to PlGF in QGP cells with siRNA-mediated knockdown of Nrp1 as compared to scrambled controls (B; scr). All data are mean±SEM (n=3-5; *p<0.05).

Chemotherapy induces PlGF expression within the neural compartment of PDAC. C, Treatment of DANG tumor bearing mice with gemcitabine induces PlGF expression released by tumor epithelial cells (human) and stromal cells (mouse) as determined using species-specific ELISA. D, Conditioned tumor cell supernatant (CM) and Gemcitabine induce PlGF expression in Schwann cells.

Blocking PlGF enhances the efficacy of chemotherapy in vivo. D, DANG tumor-bearing mice received anti-PlGF, gemcitabine (125 mg/kg, twice/week) or the combination of both, and tumor growth was monitored.

Figure 9:
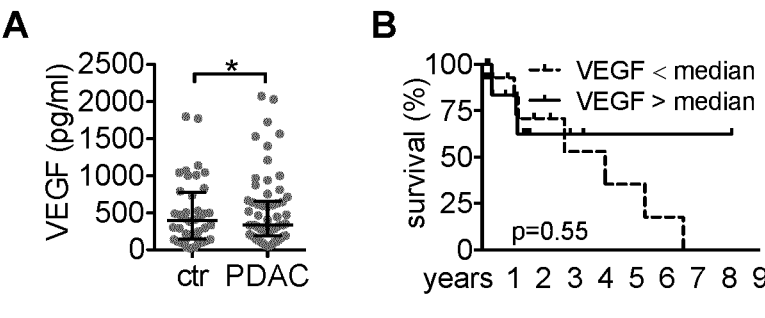
Figure 9:
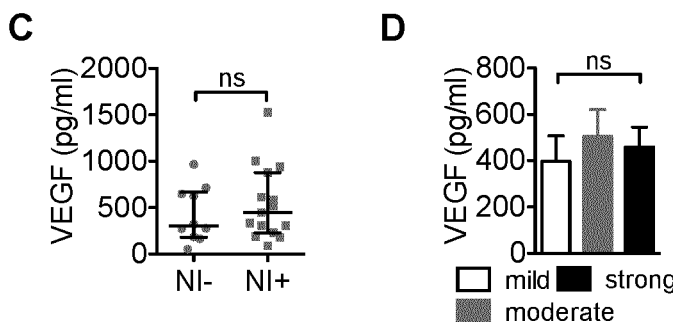

FIG. 9: VEGF is not associated with neural invasion and neuropathic pain and does not predict disease prognosis in patients with PDAC following curative-intent surgery. A, Elevated VEGF serum levels in the overall cohort of PDAC patients (n=61) as compared to healthy controls (ctr; n=40). Shown is the scatter dot plot with the median and inter-quartile range, p=0.75, Mann-Whitney test. B, Shown is Kaplan-Meier overall survival in patients with serum levels of VEGF<median (n=47) or VEGF>median (n=47), respectively, undergoing curative-intent surgery for resectable PDAC (HR: 1,44; 95% confidence interval: 0.432 to 4.7, Log-rank p=0.55). C, VEGF serum levels in patients with neural invasion (NI+; n=15) and in patients without neural invasion (NI-; n=10); p=0.53, Mann-Whitney test. D, Pain was quantified using visual analogue scales (VAS 0-10) and grouped into mild (VAS 1-3), moderate (VAS 4-6), and strong pain (VAS 7-10). Shown are mean±SEM of circulating VEGF levels in patients allocated to groups with mild (n=9), moderate (n=19) or strong pain (n=9), respectively; p=0.677.

Figure 10:
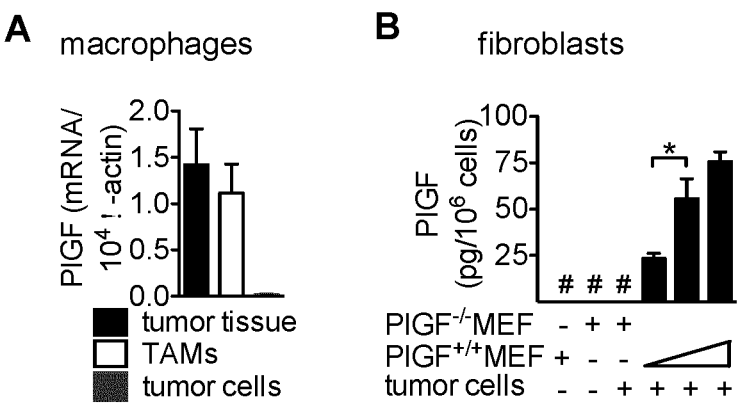
Figure 10:
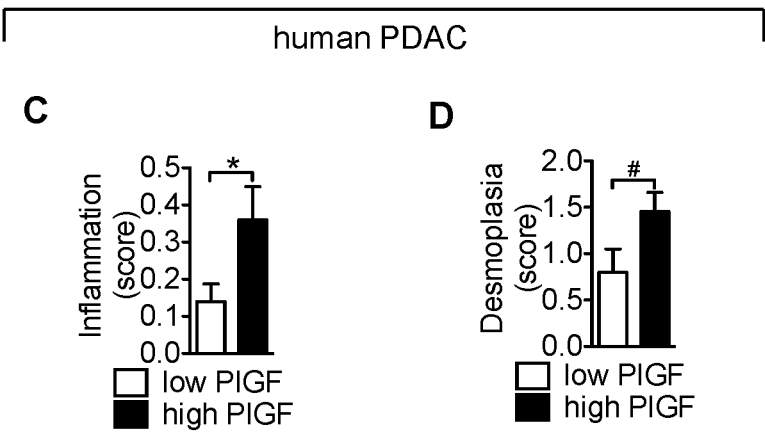

FIG. 10: PlGF mRNA transcript levels correlate with desmoplasia and inflammation within the tumor stroma. A, PlGF mRNA expression in orthotopic PDAC xenografts grown from human MiaPaca cells in NMRI$^{nu/nu}$ mice, isolated tumor-associated macrophages (TAMs) and MiaPaca cell cultures was determined using qPCR, normalized to GAPDH and shown as mean±SEM (n=3). B, In vitro expression and secretion of PlGF by mesenchymal embryonic fibroblasts (MEFs) derived from wildtype mice but not from PlGF$^{-/-}$ mice co-cultured with PDAC tumor cells. Shown is PlGF protein expression in supernatants as quantified by ELISA (n=3). C-D, Semiquantitative morphometric analysis of inflammation and desmoplasia in human PDAC specimens. Shown are inflammation (C) and desmoplasia scores (D) as mean±SEM in tumors allocated to groups with PlGF transcript levels<median or>median (n=24, *p=0.048 and #p=0.049; Mann-Whitney t-test).

Figure 11:
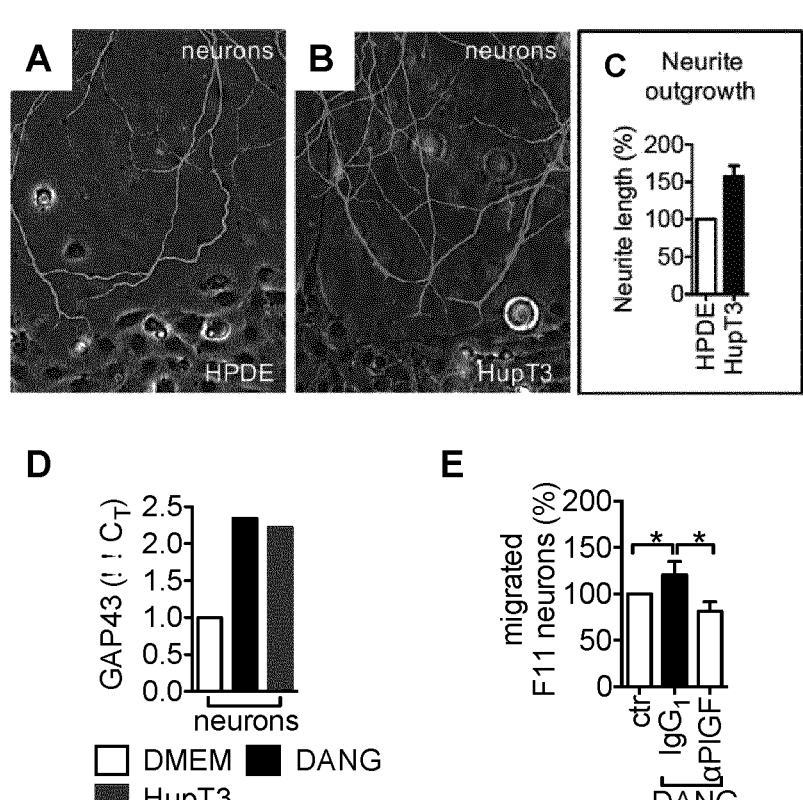

FIG. 11: PDAC stimulates neural remodelling and plasticity. A-C, Non-transformed HPDE (A) and HupT3 PDAC cells (B) were cultured in separate patches divided by a 500 μm gap using IBIDI® inserts, and nascent neurites were visualized by immunofluorescent staining for Tuj-1 following 48 h. Neurite outgrowth was quantified by determining the neurite length and shown as mean±SEM (n=3; p<0.05). D, Conditioned media from PDAC cell lines DANG and HupT3 induce expression of the growth-associated-protein (GAP)-43 in primary neurons. Shown are mean±SEM GAP43 mRNA transcript expression in primary neurons. E, Blocking PlGF in conditioned media from DANG cell cultures abrogated the directed migration of F11 neurons towards chemoattractant released from DANG cell cultures. Shown are mean±SEM (n=3; p<0.05).

FIG. 12: shows treatment scheme of patients having resectable PDAC and good clinical performance status, wherein the ratio of PlGF/sFlt1 is used for stratification of patients into different treatment groups.

Figure 13:
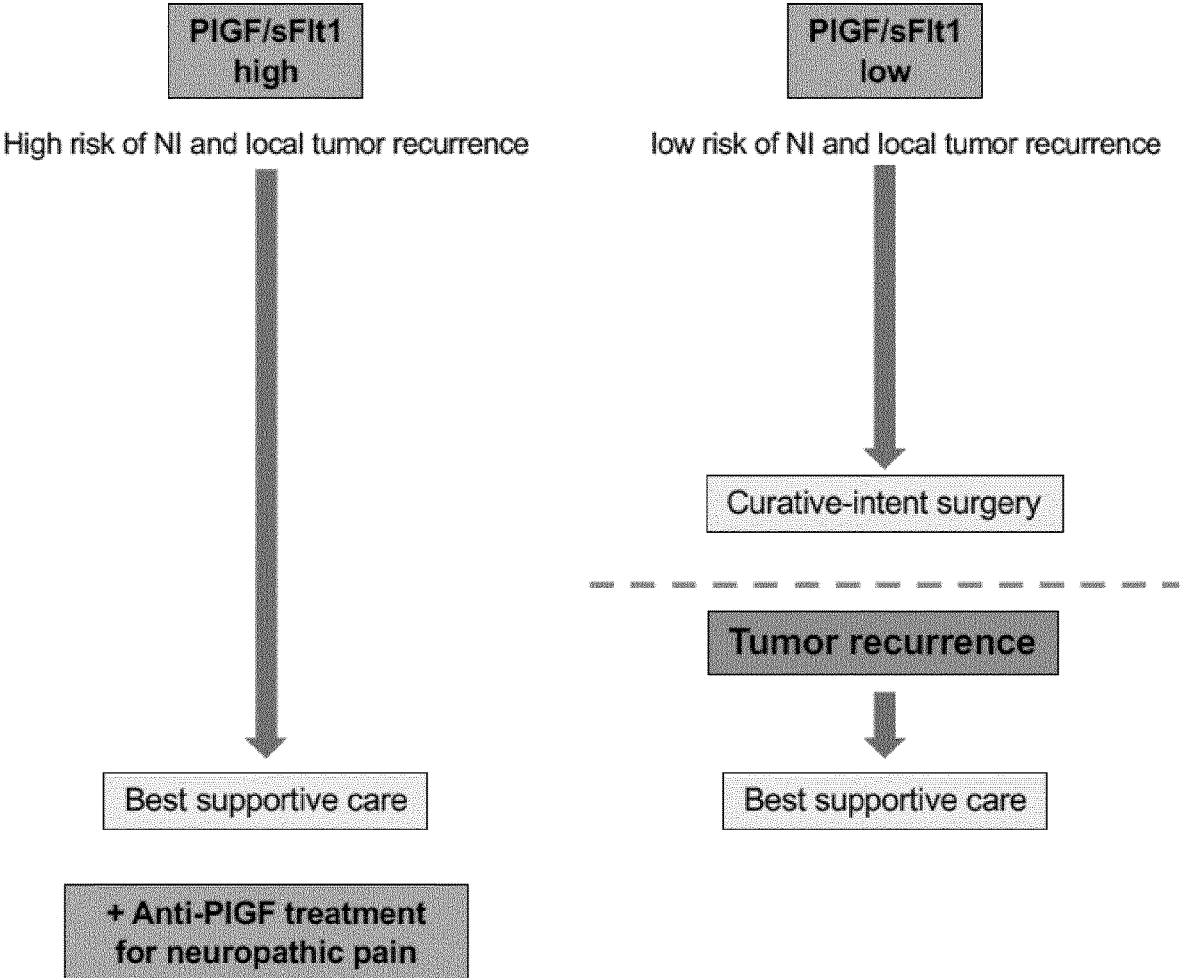

FIG. 13: shows treatment scheme of patients having resectable PDAC and bad clinical performance status and/or not eligible for chemotherapy, wherein the ratio of PlGF/sFlt1 is used for stratification of patients into different treatment groups.

FIG. 14: shows treatment scheme of patients having borderline resectable PDAC and good clinical performance status, wherein the ratio of PlGF/sFlt1 is used for stratification of patients into different treatment groups.

EXPERIMENTAL SECTION

Material and Methods

Materials

Antibodies were from ReliaTech (Braunschweig, Germany; to PlGF), Thermo Scientific (Fremont, CA; to β-actin), R&D Systems (Minneapolis, MN; to Nrp1 and VEGFR-1), and BD Pharmingen (Heidelberg, Germany; to CD31). Secondary antibodies were from Dianova (Hamburg, Germany). Recombinant human PlGF was from R&D Systems (Minneapolis, MN). Neutralizing antibodies to murine PlGF (5D11D4) and to human PlGF (16D3), as well as the IgG$_1$ control antibody (1C8011) for use in vivo were supplied by ThromboGenics (Leuven, Belgium). Quantikine® ELISA kits for human and mouse PlGF and human VEGF were from determine PlGF and VEGF were from R&D Systems (Minneapolis, MN).

Patients and Samples

Sera samples were obtained from individuals with PDAC treated at Charité-Universitätsmedizin Berlin, Department of Gastroenterology, from 1998-2018. Tumor staging with TNM classification using CT or MRT scans was performed at the time of blood sampling. In patients with locally or metastatic disease who were not applicable for surgery, histopathological diagnosis was obtained by biopsies of primary tumors or metastases. In patients who underwent curative-intent surgery histopathological diagnosis and characteristics were obtained from pathology reports and included TNM as well as grading, neural invasion, lymph node metastasis and (lymph)angioinvasion. Clinical parameters were obtained from systematic review of the medical records. Follow-up visits with imaging studies were performed at least every 3 months. Tumor progression was determined based on multi-phasic computed tomography (CT), or magnetic resonance imaging (MRI). Quantification of pain was determined using visual analogue scale (VAS 0-10), and patients were allocated to groups with no pain (VAS 0), mild pain (VAS 1-2), moderate pain (VAS 3-6) and strong pain (VAS 7-10). Healthy controls were blood donors without medical history of malignant disease and consisted of 58 women and 29 men, with a median age of 45 years (range 41-56 years).

Pancreatic Cancer Specimens

Tissue samples were from individuals undergoing surgery due to pancreatic cancer at Charité-Universitätsmedizin from 12010-2016 with histologically confirmed pancreatic adenocarcinoma.

Determination of PlGF and sFlt1 Levels in Serum and Culture Supernatants

Concentrations of PlGF and sFlt1 were determined from serum samples using Elecsys® PlGF and sFlt1 immunoassays. PlGF levels from cell culture supernatants were measured using Quantikine® ELISA kits (R&D Systems) according to the manufacturer.

Quantitative RT-PCR

RNA from forty 20 μm slices/tissue was purified using the RNeasy-mini kit (Qiagen; Hilden, Germany), and RNA concentration and quality were determined on Agilent's 2100 Bioanalyzer using the RNA-6000-Nano Kit (Agilent; Santa Clara, USA). qRT-PCR was carried out in triplicate 10 μl-reactions using PlGF and sFlt1 TaqMan primer/probes from Applied-Biosystems (Foster City, USA) with the One-Step RT-PCR Kit (Invitrogen) on a CFX96 thermo-cycler (Bio-Rad; Hercules, USA). RNA isolation and qRT-PCR of cultured cells were performed as described. Relative quantification was calculated by the Livak-method.

Immunohistochemical Analyses

Cryostat-sections were fixed in 4% PFA. Immunoperoxidase-staining was performed using Vectastain Elite ABC-kit (Vector Laboratories; Wertheim-Bettingen, Germany) and AEC as substrate chromogen (DAKO; Hamburg, Germany). The antibody to Npn1 was diluted 1:100 and was omitted in negative controls. For a semi-quantitative evaluation of immunoreactivity, the immunoreactive area was determined relative to the total field measured using AxioVision®.

Cell Lines and Cultures

For all cell lines used throughout the study, frozen stocks were generated shortly after receipt of cell lines from the repositories, or after authentication by short tandem repeat DNA-Typing. MiaPaCa, ASPC1, and Panc1 cells were from ATCC (Manassas, USA); Capan-1, Capan-2 and DANG cells were from DSMZ (Braunschweig, Germany) and maintained as described.

Preparation of Cell Extracts and Immunoblotting $5 \times 10^6$ cells were treated with doxycycline for 48 h, lysed in 100 μl RIPA buffer and immunoblotted as described. TCA-precipitates from culture supernatants were prepared as described.

Growth, Migration and Invasion Assays $10^5$ cells were plated in 24-well-dishes, and cell numbers counted using a hemocytometer. For migration assays, $2 \times 10^5$ cells/insert (doxycycline-pretreated, if applicable) were placed in serum-free medium in the upper chamber of 8 μm-Transwells (Corning) and allowed to migrate for 8-12 h towards 1% FCS added to the lower chamber. Tumor cell migration towards gradients from Schwann-cells, cultured in the lower chamber for 16 h in DMEM (0.1% BSA), and vice-versa, was determined. Migrated cells were stained with crystal-violet or DAPI and quantified by counting 5 standardized fields at 100× magnification. For 3D-Matrigel-Invasion assays, 8 μm-Transwells were coated with 1 mg/ml growth-factor-reduced Matrigel® (BD Pharmingen). Individual experiments were performed in triplicates.

Assays to Study Neural Invasion

Using transwell assays, the effect of tumor derived PlGF on the directed migration of Schwann cells (placed in the upper transwell chamber) towards chemoattractant and neurotrophic gradients released by tumor cells cultured in the lower chamber, was evaluated. Vice versa, the effect of PlGF on the directed migration of tumor cells (placed in the upper transwell chamber) towards chemoattractant and neurotrophic gradients released by Schwann cell cultures in the lower chamber, was evaluated. Antibodies to PlGF were used to neutralize PlGF. The abundance of migrated cells will be quantified as described.

Assays to Study Neural Plasticity

DRGs from newborn rats were freshly isolated and placed in 12-well plates in a growth-factor-reduced Matrigel-drop, thus providing a planar surface that enables outgrowing neurites to project and align in a 2D manner. Explanted PDAC xenograft tissues in a separate Matrigel-drop placed at 1 mm distance were connected to the DRG with a Matrigel-bridge. The matrigel layer allows gradients of chemokines and axon guidance cues to establish, and neurites to elongate towards the tumor. A matrigel drop without xenograft tumor tissue at the opposite site serves as control for random neurite outgrowth. Time-lapse imaging (Leica DM16000-B) conducted between day 1-5 following co-culture initiation was evaluated using automated acquisition software (Leica LAS AF6000). Images were taken in a chamber with closed environment at 37° C. and 5% $CO_2$ to follow neurite outgrowth. Radial distance of neurite extension from the center of the DRG were determined and calculated using ImageJ® and IBIDI® chemotaxis software.

Chemoattraction of neurons by PDAC derived neurotrophic factors was interrogated via co-culture experiments in transwell assays. Whole DRG primary cell cultures or enriched primary neurons were seeded in the upper chamber of FluoroBlok™ transwell inserts (Corning®). Filter with 1 μm pores selectively allow outgrowing neurites but not neuron cell bodies to migrate and project through the transwell membranes towards chemoattractant gradients established by tumor cells or conditioned tumor cell media, cultured or placed in the lower chamber, respectively. Of note, FluoroBlok™ inserts are provided with a light-tight polyethylene terephthalate membrane, which efficiently blocks transmission of light from the top chamber of the insert and hence allow fluorescence detection of growing neurites (CellTracker™ labeled) exclusively at the bottom side of the filter membrane. The dynamic process of neurite outgrowth and elongation in response to tumor cell gradients was captured using in vivo time-lapse microscopy imaging (every 10 minutes over 24 hours), and quantified by determining the overall number and the mean length and density of neurites at defined time points. Alternatively, primary neurons were selectively visualized by immunofluorecent detection of β3-tubulin and subjected to morphometric analysis using NeuriteQuant® to determine overall tumor length and branching. Antibodies to PlGF were used to neutralize the effect of PlGF.

In order to track locomotion of individual neurons, primary neurons were co-cultured with tumor cells in two separate patches divided by a 500 μm gap using IBIDI® inserts. GFP or cell tracking dyes (CellTracker™) were used to selectively visualize neurons and tumor cells. The dynamic process by which neurons migrate towards gradients from tumor cells were evaluated using time-lapse imaging in a Leica DMI6000B live cell microscopy unit (closed environment at 37° C. and 5% $CO_2$). Using automated acquisition software (Leica LAS AF6000), images were taken every 15 min for up to 24 h to follow cell locomotion. Cell trajectory, distance from origin, velocity, and forward migration index of neurons were calculated as described.

Tumor Models

Local authorities approved animal experiments. Female NMRI$^{nu/nu}$ mice (20-24 g) were from Charles River Laboratories (Sulzfeld, Germany). For orthotopic MiaPaCa tumors, $10^6$ cells were injected into the pancreatic head. After 7 weeks, mice were sacrificed, primary tumors harvested, and enlarged lymph nodes collected. Metastatic nodules in the mesentery were counted as described.

Statistics

Data are presented as mean±SEM, circulating levels of PlGF and sFlt1 as median with interquartile ranges. Statistical significance was determined by t-test, Fisher's exact test and Mann-Whitney test using SPSS® (v18.0; Chicago, IL) and GraphPad® Prism (v5.0; San-Diego, CA). Tumor-related survival and time-to-progression were calculated based on the date of blood sampling and analyzed using the Kaplan-Meier method and Log-rank test. Cox proportional hazards regression model was used for multivariate analysis. (*) P<0.05 values were considered significant; all tests were two-sided.

Results

Elevated Circulating PlGF/sFlt1 Serum Ratio is Associated with Neural Invasion and Predicts Disease Prognosis in Patients with PDAC PlGF is a prognostic parameter in a variety of solid cancers, as PlGF levels in blood and tumor tissues of patients reflect the risk of tumor progression and metastasis. Given that PlGF is released into systemic circulation, initial experiments assessed the expression of circulating PlGF in patients with PDAC. Since binding of PlGF to its soluble receptor Flt1 (sFlt1; sVEGFR-1) may diminish its biological activity, we also determined sFlt1 levels. The ratio PlGF/sFlt1 represents unbound and hence bioactive circulating PlGF. Compared to healthy controls, median circulating PlGF/sFlt1 ratio (from heron referred to as PlGF/sFlt1$^{circ}$) was found elevated in the overall cohort of PDAC patients (FIG. 1A), but strikingly did not differ among subgroups of patients with advanced, and thus non-resectable tumors (FIG. 1B; M1) versus locally resectable tumors prior to curative-intent surgery (FIG. 1B; R0). In sharp contrast, PlGF/sFlt1$^{circ}$ serum ratios were not elevated in patients with chronic pancreatitis (not shown).

As high rates of disease recurrence following curative-intent surgery constitute an unsolved medical need even in the absence of systemic dissemination, we analyzed the relation of PlGF/sFlt1$^{circ}$ levels to the known independent risk factors for tumor recurrence, i.e. the presence and extent of lymph node metastasis and the presence of neural invasion. Notably, PlGF/sFlt1$^{circ}$ ratios were associated with the presence of neural invasion (FIG. 1C), which represents a distinct and independent route of metastasis that is characteristic for PDAC. Indeed, median PlGF/sFlt1$^{circ}$ serum ratios are elevated to 0.32 in patients with neural invasion as compared to 0.19 in patients without neural invasion (FIG. C). In contrast, PlGF/sFlt1$^{circ}$ ratios did not correlate to the incidence (FIG. 1D) nor the extent of lymph node metastasis (not shown), which is in line with the notion that PlGF exerts a unique function as modifier at the tumor-nerve interface in PDAC.

The clinicopathological association of PlGF/sFlt1$^{circ}$ ratios with neural invasion raised the question, whether serum ratios of PlGF/sFlt1$^{circ}$ also reflected the prognosis. Accordingly, patients were grouped by high (>50$^{th}$ percentile) or low (≤50$^{th}$ percentile) levels of PlGF/sFlt1$^{circ}$ ratios, respectively, and Kaplan-Meier curves based on survival were generated. Indeed, PlGF/sFlt1$^{circ}$ levels >50$^{th}$ percentile (>median) were associated with poor prognosis and predicted shorter overall survival in patients with PDAC undergoing curative-intent surgery (FIG. 1E). Notably, in patients with unresectable advanced or metastatic PDAC (representing palliative disease) PlGF/sFlt1$^{circ}$ levels were not associated with overall survival (FIG. 1F), but with neuropathic pain (FIG. 1G), which is closely associated with the extent and severity of neural invasion in PDAC. In sharp contrast, circulating levels of VEGF did not differ in patients with PDAC as compared to healthy controls, nor were they associated with lymph node metastasis, neural invasion, overall survival, or pain (Suppl. FIG. 1).

In an attempt to stratify patients to prognostic subgroups, optimal cut point and ROC analyses were performed and displayed 92.0% sensitivity and 85.0% specificity for the discrimination between patients with neural invasion and patients without neural invasion at a cut-off PlGF/sFlt1$^{circ}$ serum ratio of 0.2404 (FIG. 2).

PlGF and its Receptor Nrp1 are Expressed at the Tumor-Nerve Interface in PDAC

Consistent with elevated PlGF/sFlt1$^{circ}$ serum ratios in PDAC patients, PlGF mRNA expression was induced in tissues of human PDAC (FIG. 3A) and mouse orthotopic xenograft tumors (FIG. 3B, and own previous data) as compared to healthy pancreas adjacent to the tumor. Moreover, differential quantification of mouse and human PlGF proteins in xenograft tumor tissues (FIG. 3B) and human PDAC cell lines (FIG. 3C) using species-specific ELISA identified both, the epithelial tumor cells as well as the stromal compartment as source for PlGF production.

Indeed, while PlGF expression and secretion was found either deficient or variably present in a series of human PDAC cell lines in vitro (FIG. 3C), stromal tumor associated macrophages (TAMs), which were isolated from MiaPaCa xenograft tumor tissues, constituted a major source of PlGF mRNA production in xenografted mouse tumors (Suppl. FIG. 2A).

In addition to TAMs, the stromal tumor micromilieu consists of a variety of different cell types, of which fibroblasts, Schwann cells and neurons have particularly been characterized to play a pivotal role in PDAC progression and neural metastasis. Notably, in in vitro co-culture experiments, PDAC cells induced the expression of PlGF in mesenchymal embryonic fibroblasts (MEFs) derived from wildtype mice but not from PlGF$^{-/-}$ mice (Suppl. FIG. 2B). These finding are consistent with our observation that high levels of PlGF mRNA transcripts in human PDAC specimens correlate with increased inflammation and desmoplasia of the tumor stroma (Suppl. FIG. 2C-D) and hence fit the pleiotropic role of PlGF as modulator of the tumor microenvironment. Moreover, conditioned supernatants from PDAC cell cultures were capable to induce PlGF expression in primary Schwan cells, but not in primary neurons (FIG. 3D).

On the receptor side, we focused on Nrp1, which acts as independent receptor for PlGF and conveys signals different from established VEGFR1-mediated signaling pathways. Nrp1 immunoreactivity was localized to epithelial tumor cells, parenchymal nerves and on vascular endothelial cells in human PDAC tissues (FIG. 3E), but weakly expressed in healthy pancreas (FIG. 3F). Similarly, non-transformed immortalized human pancreatic ductal epithelial cells (HPDE) lack Nrp1 mRNA and protein expression, which contrasts with abundant Nrp1 mRNA transcripts and protein levels in most PDAC cell lines (FIG. 3G). Notably, Nrp1 mRNA expression was also present in dorsal root ganglia, primary neurons and Schwann cells, freshly isolated from newborn mice or rats (FIG. 3H), as well as in permanent F11 neuron cell cultures (not shown).

In contrast to Nrp1, expression of VEGFR-1 appeared restricted to the stromal compartment of PDAC, and in particular localized to vascular endothelial cells, inflammatory cells and parenchymal nerves (own previous results and not shown). In line with this observation, VEGFR-1 transcripts were rarely expressed among human PDAC cell lines (FIG. 3G), but present in DRGs, primary and F11 neurons as well as Schwann cells (FIG. 3H; and not shown). VEGFR-1 mRNA transcripts were furthermore induced in primary neurons upon cultivation in conditioned media from PDAC cell lines (not shown), consistent with previous findings that expression of VEGFR-1 in nerves was induced in PDAC patients.

Hence, both epithelial tumor cells and the neuronal compartment of the tumor stroma have the capacity to respond to secreted PlGF ligand.

Neural Invasion of Extratumoral Nerves Predicts Early Disease Recurrence in PDAC In routine pathology reports, presence of neural invasion is described as a solely qualitative feature in up to 90% of tumors. To obtain a quantitative description of neural invasion (referred to as NI) and neural plasticity, we implemented a histomorphometric analysis which allows recording a detailed set of histomorphological parameters.

These parameters are based on evaluation of 30 $mm^2$ areas within the tumor (referred to as intratumoral) and in healthy tissue adjacent to the tumor margin (referred to as extratumoral), and include (i) nerve number (density) and diameters (hypertrophy), (ii) presence, quality (perineural vs. intraneural) and area of tumor cell invasion, (iii) presence of intraneural and tumoral inflammation and presence of desmoplasia.

As expected, thorough morphometric evaluation of PDAC specimens revealed that intratumoral NI is present in almost all PDAC patients (FIG. 4A), while the extent of intratumoral NI as quantified by determining the fraction of tumor-invaded nerves per total nerves largely varied among PDAC patients (FIG. 4B), as did the extent of neural plasticity (not shown).

Mechanistically, migration of tumor cells along nerves represents a process which may ultimately result in the continuous spread of tumor cells beyond the boundaries of the tumor. Hence, NI can occur in nerves within normal pancreatic regions distant to the tumor by means of continuous spread of tumor cells along parenchymal nerves. In addition to determining NI in tumor tissues, we thus also quantified NI in respective healthy pancreatic tissues adjacent to the tumor margin (referred to as extratumoral NI). Although extratumoral NI was significantly less frequent as compared to intratumoral NI, when paired tumor and healthy tissues were analyzed, its incidence remained high (FIG. 4A-B).

Clinically, the extent of extratumoral NI correlated with an unfavorable course of the disease and early disease recurrence in PDAC patients. Indeed, when patients who underwent curative-intent surgery for PDAC were grouped by a high or low neural invasion score, and Kaplan-Meier curves based on disease-free survival (DFS) and overall survival were generated, a high neural invasion score (score 2) was associated with shorter disease-free survival (FIG. 4C) and overall survival (FIG. 5A) as compared to a low neural invasion score (score 0/1). More specifically, a thorough quantitative analysis of extratumoral nerves linked a high fraction of tumor-invaded nerves per total nerves to shorter disease-free survival (FIG. 4D) and overall survival (FIG. 5B).

Tumor cell invasion of the intraneural space (referred to as Intraneural invasion) is considered a feature of advanced neural invasion in PDAC. Accordingly, both the presence of intraneural invasion and a high fraction of intraneural invasion of extratumoral nerves predicted early disease recurrence and shorter overall survival in our patients' cohort (FIG. 4E-F and FIG. 5C-D).

Thus, we are able to quantitatively score the extent of NI of extratumoral nerves and accordingly stratify patients with PDAC into prognostic subgroups.

Expression of PlGF Transcripts Correlates with the Extent of Neural Invasion of Extratumoral Nerves and with Neural Plasticity Given that expression of PlGF and its receptors Nrp1 and VEGFR1 are present and/or increased in cellular compartments of the tumor-nerve interface in PDAC, we aimed to determine, whether PlGF transcript levels correlate with neural invasion. Since incidence of neural invasion in intratumoral nerves was high among PDAC patients (FIG. 4A-B), morphometric analysis was mainly focused on neural invasion of extratumoral nerves (FIG. 6A), which is considered an advanced stage of neural spread of tumor cells, and which we found closely linked to disease-free and overall survival in PDAC patients (FIG. 4C-F and FIG. 5A-D). Indeed, tumors with extratumoral NI exhibited higher mean PlGF transcript levels as compared to tumors, in which extratumoral NI was absent (FIG. 6B). Moreover, PlGF transcript levels correlated with the incidence of NI of extratumoral nerves, and all tumors with PlGF transcript levels >median exclusively displayed presence of NI within extratumoral nerves (FIG. 6C). A more detailed morphometric analysis addressed the correlation of PlGF transcript levels with features of advanced and more severe NI. Such features are an extended circumferential range of perineural nerve invasion and the presence of tumor cell invasion within the intraneural space, referred to as intraneural nerve invasion (FIG. 6A). Thus, tumors with perineural invasion of extratumoral nerves pe se exhibited higher mean PlGF transcript levels as compared to tumors without perineural invasion (FIG. 6D), whilst tumors with a high perineural invasion score, based on determining the extent of circumferential perineural nerve invasion, exhibited PlGF transcript levels>median (FIG. 6E). Finally, PlGF transcript levels>median were linked to a higher fraction of intraneural invasion of extratumoral nerves (FIG. 6F). Accordingly, intraneural nerve fraction of intratumoral nerves was also higher in tumors with PlGF mRNA transcript expression>median (n=24, p=0.0133; Mann-Whitney test) as compared to tumors with PlGF mRNA<median. Furthermore, the overall nerve area in tumors with PlGF mRNA transcript levels>median was larger as compared to tumors with PlGF mRNA transcript levels <median, delineating a role of PlGF as modifier of neural plasticity in PDAC (FIG. 6G). In contrast, PlGF mRNA transcript levels did not correlate with the incidence (FIG. 6H) nor the extent of lymph node metastasis (FIG. 6I) in these patients.

PlGF Mediates Mutual Chemoattraction Between Tumor Cells and Schwann Cells

Schwann cells act as conduits that facilitate the subsequent axonal outgrowth in neuronal regeneration following injury and in neural invasion. More recent reports in PDAC revealed, that Schwann cells have the capacity to temporarily disengage from the perineural sheath and migrate towards tumor cell colonies, and reciprocally chemoattract tumor cells into the direction to the nerve, altogether promoting NI.

To determine the consequences of PlGF for mutual chemoattraction of Schwann cells and tumor cells within the stromal microenvironment, we initially used monolayer cultures and conditioned supernatants of DANG cells with endogenous expression of PlGF as chemoattractant. Conditioned media from DANG cell monolayers enhanced the directed migration of Schwann cells, while inhibition of PlGF by using anti-PlGF, but not control IgG$_1$ antibodies abrogated this effect (FIG. 7A). Vice versa, conditioned supernatant from Schwann cell cultures stimulated the directed migration of Panc1 (FIG. 7B) and Capan-2 tumor cells (FIG. 7C), while blocking PlGF using anti-PlGF antibodies abolished the directed migration of PDAC cells towards chemoattractant released by Schwann cells (FIG. 7B-C). Thus, PlGF affects the chemotactic profile of PDAC cells and Schwann cells, suggesting that PlGF modifies NI in models of PDAC.

PDAC Xenograft Tissues and Gradients From PDAC Cells Stimulate Neurite Outgrowth To assess neural plasticity in PDAC, we performed ex vivo co-culture assays using xenograft PDAC tissue or cell lines, respectively, which were co-cultured with whole DRGs, as well as single cell cultures of primary neurons and Schwann cells, both freshly isolated from newborn rat and mouse DRGs, and permanent cultures of F11 hybridoma neurons.

When DRGs are cultured in 3D collagen matrices together with (matrix embedded) explants of PDAC xenograft tissues, neurite outgrowth is skewed towards the tumor tissue, as reflected by differences in the radial distance of neurite extension from the center of the DRG (FIG. 7D). Thus, neurites facing the tumor were more elongated than neurites at the opposite site of the DRG, suggesting that tumor gradients stimulate and/or attract neurite outgrowth and elongation.

To study the directed chemoattraction of nascent neurites towards PDAC gradients, neurons were co-cultured with either human pancreatic ductal epithelial cells (HPDE) or PDAC cells in separate patches divided by a 500 μm gap using IBIDI® inserts (Suppl. FIG. 3A-C), and nascent neurites were visualized by immunofluorescent staining for Tuj-1 following 48 h. Notably, neurite outgrowth as quantified by determining the neurite length was increased over time when neurons were co-cultured with HupT3 tumor cells as compared to non-transformed HPDE cells. Moreover, conditioned media from PDAC cell lines induce expression of the growth-associated-protein (GAP)-43 in primary neurons (Suppl. FIG. 3D), which stimulates growth cone formation and neurite outgrowth. Thus, PDAC derived tissue and growth factors have the capacity to induce neural remodeling in ex vivo models of the tumor-nerve interface.

Tumor Derived PlGF Regulates Neural Plasticity

To gain a more complex depiction of tumor induced changes of neuronal plasticity and to interrogate chemoattraction of neurons by PDAC derived neurotrophic factors, whole DRG primary cell cultures were incubated with supernatants from PDAC cell lines. Since evidence is emerging that nerve plasticity is controlled by mutual interaction of neurons with their ensheathing Schwann cells, we used whole DRG primary cell cultures (encompassing Schwann cells in addition to primary neurons) instead of using pure (highly enriched) cultures of primary DRG neurons. Primary neurons are selectively visualized by immunoflourecent detection of β3-tubulin and subjected to morphometric analysis using NeuriteQuant®.

PDAC cell supernatants variably stimulated overall neurite length (FIG. 7E), as did recombinant PlGF and the two major known neurotrophic factors, nerve growth factor (NGF) or glial-derived neurotrophic factor (GDNF; FIG. 7F).

Importantly, neutralizing endogenous PlGF in conditioned media from DANG cell cultures with anti-PlGF antibodies reduced neurite length (FIG. 7F-I). Moreover, blocking PlGF in conditioned media from DANG cell cultures also abrogated the directed migration of F11 neurons towards chemoattractant released from DANG cell cultures (Suppl. FIG. 3E). Together, these data suggest, that tumor derived PlGF has the capacity to modify cancer-mediated neural plasticity and neural remodeling.

PlGF Stimulates Colony Formation of Tumor Cells Via Nrp1

Pharmacological studies using anti-PlGF have previously revealed a functional role of PlGF for tumor growth and metastases in syngeneic orthotopic PDAC mouse models. More recently, Nrp1 has emerged as independent receptor for PlGF and conveys signals different from established VEGFR1-mediated signaling pathways. However, the role of Nrp1 for PlGF mediated effects in PDAC epithelial cells has not been assessed yet. Therefore, we experimentally studied the consequences of exogenous PlGF and antibody-based pharmacological inhibition of PlGF, respectively, on colony formation of PDAC cells. Notably, anti-PlGF antibodies prevent biding of PlGF to both, VEGFR-1 and Nrp1, as previously reported.

In vitro, regulation of clonal growth of PDAC and pancreatic neuroendocrine tumor cells by PlGF was critically dependent on Nrp1. Thus, exogenous PlGF stimulated colony formation of Nrp1-expressing Capan-1 and QGP cells irrespective of VEGFR1 deficiency of QGP cells, but not of MiaPaCa cells, lacking both VEGFR1 and Nrp1 (FIG. 8A). Conversely, pharmacological disruption of autocrine PlGF stimulation using neutralizing anti-PlGF antibodies in VEGFR1-deficient Panc1 and BXPC3 cells reduced clonal growth (FIG. 8A and FIG. 3G). Moreover, knockdown of Nrp1 in VEGFR1-deficient QGP-1 cells abrogated the response to PlGF, while neutralizing endogenous PlGF in DANG cells reduced clonal growth equal to knockdown of the Nrp1 receptor (FIG. 8A-B). Given the overall rare expression of VEGFR-1 in PDAC cell lines (see FIG. 3G), these data indicate that interaction of PlGF with Nrp1-receptor may be required and sufficient to mediate effects PlGF on clonal growth of PDAC.

Blocking PlGF Enhances the Efficacy of Chemotherapy In Vivo

Treatment of mice with DANG xenograft tumors with the cytostatic agent gemcitabine increased PlGF expression in tumor epithelial cells and the stromal compartment of PDAC xenografts (FIG. 8C). Moreover, exposure of primary neurons and Schwann cells with conditioned tumor cell media or gemcitabine dose-dependently increased PlGF expression in Schann cells, but not in primary neurons (FIG. 8D), altogether providing a rationale to test whether blocking PlGF would enhance chemotherapeutic treatment. Indeed, combination therapy with anti-PlGF and gemcitabine inhibited growth of DANG xenograft tumors more than monotherapies alone (FIG. 8E). Thus, blocking PlGF may enhance the efficacy of chemotherapy.

Discussion

Understanding the molecular basis of the almost inevitable, therapy-refractory progression of PDAC constitutes a central task for translational research. Our work applies the paradigm of the neurovascular link to understand how tumor cells exploit the shared evolutionary origin of axon-/vessel guidance factors in specialized interactions with nerves (and vessels) in the tumor environment and explores PlGF as a member of the axon and vessel guidance family for such specialized interactions in PDAC.

Our current data provide evidence, that elevated circulating PlGF levels are associated with neural invasion (NI) and shorter survival in patients with PDAC who underwent surgery, and delineate the function of PlGF for neural invasion, which represent the clinically relevant and characteristic route of metastatic spread in PDAC. Experimentally, we characterize PlGF in its unique role as an axon guidance factor, which supports neural plasticity on one hand, and attracts tumor cells towards nerves on the other hand. Specifically, we provided evidence that PlGF contributes to induction of directional and dynamic changes in outgrowth of primary DRG neurons upon exposure to PDAC derived guidance cues and growth factors and supports mutual chemoattraction of tumor cells with neuronal cells and Schwan cells, respectively.

Ultimately, findings from these experimental models translated to the clinical observation that circulating PlGF/sFlt1$^{circ}$ serum ratios are associated with NI. More specifically, induction of tumor PlGF mRNA transcript levels correlated to higher incidence and more specifically to an increased extent of extratumoral NI, which predicted unfavorable prognosis, early disease recurrence and reduced survival in patients with PDAC following curative-intent surgery.

The neurovascular link offers a unique concept to recognize specialized features in the characteristic way of cancer cell spread along nerves in PDAC. Physiologically, nerves and vessels exhibit comparable structural patterning and share similar ligand-receptor cues to navigate to their target. So called axon guidance factors have originally been characterized in neurogenesis to function as molecular cues, which control growth, navigation and positioning of neurons in the developing brain. These ancient axon guidance signals from the evolutionary older nervous system were co-opted for navigational control by the emerging younger blood vessels. In turn, VEGF-A, which was originally discovered as the key angiogenic growth factor, has recently been characterized as neurotrophic factor in brain development and motoneuron diseases.

Own previous work provided precedent evidence for a role of axon guidance factor Slit2 and its receptor Robo1 in NI of PDAC, hence creating a functional counterpart to the report of frequent genomic mutations in the Slit2-Robo pathway. Indeed, reduced expression of components of this pathway correlated to shorter survival in PDAC. Restoring Slit2 function in PDAC cell lines inhibited bidirectional chemoattraction of tumor cells, neurons and Schwann cells, and impaired accelerated directional PDAC cell navigation along outgrowing neurites.

VEGF-A binds to and signals via two receptor tyrosine kinases, VEGFR-1 and VEGFR-2, which are highly homologous in their structure, but convey distinct and independent biological functions. In contrast, PlGF, a homologue member of the VEGF growth factor family, exclusively binds to VEGFR-1. A recent report established a role of VEGFR1 in cancer related functional and structural remodeling of nerves under pathophysiological conditions of neuropathic pain: Indeed, VEGF and its homologue PlGF induced nociceptive sensitization and augmented pain sensitivity through selective activation of VEGFR-1 (but not VEGFR-2), expressed in sensory neurons in human cancer and mouse models. Moreover, VERGR1 expression and intensity were upregulated in sensory nerves of human PDAC specimens and correlated to perceived pain intensity in PDAC patients. Conversely, genetic loss or pharmacological inhibition of VEGFR1 signaling or VEGF ligands, respectively, impaired tumor associated sprouting and hypertrophy of nerve fibers and attenuated cancer associated pain in animal models.

In perfect line with these observations, our current data correlate circulating serum levels of PlGF with perceived neuropathic pain in PDAC patients and more specifically characterize a functional role of PlGF in cancer related structural remodeling of neural plasticity. Thus, PlGF transcript levels correlated with the overall nerve area in PDAC, and blocking PlGF by anti-PlGF antibodies abrogated cancer mediated neurite outgrowth from primary DRG neurons in ex vivo co-culture models, and hence reduced neural remodeling and plasticity.

Furthermore, our experimental and clinical data assign to PlGF a novel function in the control of neural invasion by modifying bilateral chemoattraction between PDAC cells and neuronal cells, in particular Schwann cells, which recently gained increasing attention as key players in NI of PDAC.

A recent systemic review and meta-analysis advocates NI as independent prognostic factor for tumor recurrence (disease free survival) and overall survival in patients with PDAC in multivariate analysis. Median survival ranged from 7 to 28.5 months for patients with presence of NI versus 8 to 56.1 months for patients, in whom NI was absent. Fittingly, a retrospective analysis in our department characterized NI as an unfavorable prognostic factor with a reduced median survival of 31 months in patients with NI as compared to 79.3 months in patients without NI.

Despite the utmost clinical impact of NI, neither quantification of NI nor the assessment of extratumoral (intrapancreatic) neural invasion has been implemented as standardized procedures in histopathological reports, taking into account that NI frequently occurs in nerves within normal pancreatic regions distant to the tumor (referred to as extratumoral NI).

So far, only few studies provide sufficient information on extratumoral (intrapancreatic) NI, with incidences ranging from 76.2% to 97.8%. Accordingly, our current data support further evidence that the severity of extratumoral NI (as determined by the fraction of invaded nerves per total nerves) is associated with reduced survival in PDAC patients and are thus in perfect agreement with published data, which characterized extratumoral neural invasion as an independent, unfavorable prognostic parameter for tumor recurrence and survival in PDAC patients.

A thorough morphometric and quantitative analysis of NI and neural plasticity now enabled us to characterize PlGF in its role as axon guidance cue by correlating PlGF transcript levels in PDAC tissues with the extent of intra- and extratumoral neural invasion. Thus, induced expression of PlGF transcripts in PDAC specimens correlated with a higher extent of extratumoral NI. Apart from signaling via VEGFR-1, the axon guidance receptor, neuropilin-1 was found to acts as independent receptor for PlGF and conveys signals different from established VEGFR1-mediated signaling pathways. As both receptors are expressed in the neuronal compartment of PDAC and moreover high expression of Nrp1 was associated with poor overall survival in patients following resection of PDAC, it is tempting to speculate that both, VEGFR-1 and Nrp1 mediate observed effects of PlGF on neural plasticity and neural invasion.

Taken together, our experimental and clinical data assign to PlGF a novel function in the control of neural invasion by modifying bilateral chemoattraction between PDAC cells and neuronal cells at the tumor-nerve interface. More specifically, our data suggest, that blocking PlGF may represents a promising therapeutic strategy to impair metastatic spread along outgrowing neurites and hence to reduce tumor recurrence rates and improve survival following curative-intent surgery in the subgroup of PDAC patients with elevated PlGF/sFlt1$^{circ}$ serum ratios.

Upfront tumor resection with following adjuvant chemotherapy has long been the standard of care of patients with resectable tumors. However, despite major improvement of surgical quality, nearly half of patients fail to complete or never receive adjuvant chemotherapy after pancreatectomy, due to postoperative complications, clinical deterioration with poor clinical performance status and limited compliance, or early progressive disease. Especially those patients who are not able to receive adjuvant chemotherapy have a poor prognosis.

This has led to an ongoing paradigm shift and resulted in an increased emphasis on the use of upfront neoadjuvant chemotherapy for all patients without evidence of metastatic disease. Neoadjuvant chemotherapy, given upfront to surgery, has emerged as standard therapy in a variety of cancer entities including breast cancer, esophagogastric cancer and colorectal cancer, and has several potential benefits in pancreatic cancer as well: such as early treatment of occult (distant or nodal) micro-metastases, improved compliance with chemotherapy and early delivery of systemic chemotherapy to all patients, the potential to downstage tumor size and increase margin-negative (R0) resection rates, as well as select patients who respond to neoadjuvant treatment and are thus likely to benefit from surgery, whilst preventing vain surgery in patients with rapidly progressive disease. Given these advantages, there is an increasing clinical focus on evaluating the use of neoadjuvant therapy in the upfront resectable pancreatic cancer population. The neoadjuvant approach has recently been supported by three randomized controlled trials, which showed a favorable outcome of neoadjuvant gemcitabine or gemcitabine-based chemoradiotherapy versus upfront surgery. Indeed, neoadjuvant therapy decreases nodal positivity, increases margin-negative resection rates and increases overall and disease-free survival. Since FOLFIRINOX has proven superior compared to gemcitabine in both the metastatic and adjuvant setting, it is likely to be a more effective neoadjuvant regime as well. Several ongoing randomized clinical trials hence currently evaluate the efficacy of neoadjuvant FOLFIRINOX given either alone or combined with radiotherapy in comparison to gemcitabine-based regimens.

It is widely appreciated that neural invasion (NI) limits the clinical benefit of surgery followed by adjuvant therapy.

So far however, neural invasion has not been systematically evaluated yet in the neoadjuvant therapeutic concept. Given the ongoing paradigm switch to neoadjuvant therapy, understanding the mechanisms underlying neural invasion as a unique and characteristic route of local tumor cell spread in pancreatic cancer has therefore become a major task to understand limitations of neoadjuvant therapeutic regimens and consecutively better direct treatment stratification of patients with pancreatic cancer.

Own data provide evidence that incidence and extent of NI of extratumoral nerves strongly correlate to disease prognosis, in particular to time-to-disease-recurrence. However, pathologic analysis to determine NI inevitably requires histology on resected tumor tissue and cannot be addressed on biopsy material only. Thus, neoadjuvant therapy upfront to surgery precludes from determining NI on therapy-naïve tissue and consequently lacks the access to essential prognostic tissue parameters (i.e. neural invasion status).

Circulating PlGF and sFlt1, and hence PlGF/sFlt1$^{circ}$ serum ratios, are easily accessible biomarkers which can be repeatedly quantified in the serum of PDAC patients in routine laboratory tests. Since PlGF/sFlt1$^{circ}$ in the serum of PDAC patients correlate with NI in pancreatic cancer, they can be used as serum biomarkers to predict the risk of NI and to allow identifying those patients with high risk of NI, who will benefit from neoadjuvant therapy and/or anti-PlGF targeted therapy by reducing NI upfront to surgery. Current optimal cut point and ROC analyses bases on our PDAC patients' cohort now determined a cut-off PlGF/sFlt1$^{circ}$ serum ratio of 0.2404, which allows for discrimination between patients without neural invasion and patients with neural invasion at 92.0% sensitivity and 85% specificity and therefore enables to allocate PDAC patients to prognostic and therapeutic subgroups.

It is a matter of ongoing debate to what extent neoadjuvant chemotherapy reduced NI, but recent clinical evidence suggests that this effect might be limited. Indeed, neoadjuvant chemotherapy prolongs DFS primarily by increasing time to recurrence of distant metastasis while effects on local recurrence rate and time to local disease recurrence are minor.

Own data provide evidence that chemotherapy in turn induces expression of PlGF in Schwann cells, and PlGF supports survival and clonal growth of tumor cells (even under conditions of chemotherapeutic treatment), the tumor-nerve interface might be considered as a microenvironmental niche within the tumor stroma, which protects tumor cells from chemotherapeutic treatment and therefore facilitates further metastatic spread of PDAC. Blocking PlGF might therefore constitute a beneficial adjunct to neoadjuvant or adjuvant treatment modalities which (i) prevents PlGF-mediated escape from chemotherapy, (ii) increases efficacy of neoadjuvant chemotherapy and (iii) thereby reduces NI within the tumor cell-neural niche, (vi) ultimately resulting in lower local tumor recurrence rates and improving the hitherto devastating prognosis of pancreatic cancer.

What is claimed is:

1. A method for identifying neural invasion in a patient with pancreatic ductal adenocarcinoma (PDAC), the method comprising the steps of:
   a) determining in a sample from a PDAC patient the expression levels of placental growth factor (PlGF) and soluble Fms-related tyrosine kinase 1 (sFlt1);
   b) calculating a ratio of the expression levels of PlGF and sFlt1, wherein the expression level of PlGF is either the numerator or the denominator of the ratio;
   c) determining presence of neural invasion in said PDAC patient if the ratio in b) is deviated from a ratio from a reference sample or a predetermined threshold value; and
   d) administering to the PDAC patient a specific therapy; wherein the specific therapy comprises partial or full tumor resection, neoadjuvant chemotherapy, neoadjuvant radiation therapy, adjuvant chemotherapy, adjuvant radiation therapy, an anti-PlGF therapy, palliative therapy, and/or palliative pain therapy; and wherein the PDAC patient is eligible to receive neoadjuvant or adjuvant therapy.

2. The method according to claim 1, wherein the deviation, when the ratio is calculated using the expression level of PlGF in the numerator, is an increase in the ratio of the patient sample compared to the reference sample or the predetermined threshold value and/or wherein the deviation, when the ratio is calculated using the expression level of PlGF in the denominator, is a decrease in the ratio of the patient sample compared to the reference sample or the predetermined threshold value.

3. The method according to claim 1, wherein the ratio between the expression levels of PlGF and sFlt1 is calculated using the metric [PlGF/sFlt1] or the metric [sFlt1/PlGF].

4. The method according to claim 1, wherein, when the ratio is calculated using the expression level of PlGF in the numerator, the predetermined threshold value is from 0.15 to 0.35.

5. The method according to claim 1, wherein, when the ratio is calculated using the expression level of PlGF in the denominator, the predetermined threshold value is from 6.67 to 2.86.

6. The method according to claim 1, wherein the sample from the PDAC patient is or is derived from a tissue sample or a body fluid.

7. The method according to claim 1, wherein the expression levels of PlGF and sFlt1 are determined using PCR or an immunological method.

8. The method according to claim 1, wherein the PDAC patient has not yet undergone partial or full resection of said PDAC.

9. A method of determining responsiveness of a PDAC patient to an anti-PlGF therapy, the method comprising the steps of:

a) determining in a sample from the PDAC patient the expression levels of placental growth factor (PlGF) and soluble Fms-related tyrosine kinase 1 (sFlt1);

b) calculating a ratio of the expression levels of PlGF and sFlt1, wherein:

i) the ratio is calculated using the expression level of PlGF in the numerator; or ii) the ratio is calculated using the expression level of PlGF in the denominator;

c) determining a deviation of the ratio in b) from a ratio of a reference sample or a predetermined threshold value, wherein:

in i) the ratio of PlGF expression level to sFlt1 expression level is above the ratio from the reference sample or threshold value; or in ii) the ratio of sFlt1 expression level to PlGF expression level is below the ratio from the reference sample or threshold value; and d) administering to the patient an anti-PlGF therapy.

10. A method of determining whether a PDAC patient will benefit from partial or full tumor resection, the method comprising the steps of:

a) determining in a sample of the patient the expression level of placental growth factor (PlGF) and soluble Fms-related tyrosine kinase 1 (sFlt1);

b) calculating a ratio of the expression levels of PlGF and sFlt1, wherein:

i) the ratio is expressed using the expression level of PlGF in the numerator; or ii) the ratio is expressed using the expression level of PlGF in the denominator;

c) determining a deviation of the ratio of the patient sample from a ratio of a reference sample or a predetermined threshold value, wherein:

in i) the ratio between expression levels of PlGF and sFlt1 is above the reference sample or threshold value; or in ii) the ratio between expression levels of PlGF and sFlt1 is below the reference sample or threshold value; and d) administering to the PDAC patient in-hospital supportive care and withholding partial or full tumor resection;

wherein the PDAC patient is ineligible to receive neoadjuvant or adjuvant therapy.

11. An anti-PlGF compound for use in the method of claim 1 or claim 9 in the treatment of a PDAC patient, wherein, when the ratio of the expression levels of PlGF and sFlt1 in a sample from said patient is calculated using the expression level of PlGF in the numerator, said PDAC patient has an increase in the ratio relative to the ratio of a reference sample or a predetermined threshold value of 0.22, 0.23, 0.24 or 0.25.

12. The method of claim 1 or 9, wherein the anti-PlGF therapy comprises: a) an anti-PlGF compound or b) an anti-PlGF antibody comprising six CDR regions corresponding to the sequences of SEQ ID NO: 1 to 6.

13. The method according to claim 4, wherein the predetermined threshold value is from 0.2 to 0.3 or from 0.22 to 0.26.

14. The method according to claim 5, wherein the predetermined threshold value is from 5 to 3.33 or from 4.55 to 3.85.

15. The method according to claim 6, wherein the sample from the PDAC patient is, or is derived from, a body fluid, serum, plasma and/or urine.

16. The method according to claim 7, wherein the immunological method comprises an ELISA.

* * * * *

SEQUENCE LISTING

<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic

```
                peptide
<220> FEATURE:
<223> OTHER INFORMATION: CDR1 heavy chain

<400> SEQUENCE: 1

Gly Tyr Thr Phe Thr Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 heavy chain

<400> SEQUENCE: 2

Ile Tyr Pro Gly Ser Gly Asn Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 heavy chain

<400> SEQUENCE: 3

Val Arg Asp Ser Pro Phe Phe Asp Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 light chain

<400> SEQUENCE: 4

Gln Ser Leu Leu Asn Ser Gly Met Arg Lys Ser Phe
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 light chain
<220> FEATURE:
<221> NAME/KEY: MOD_RES
<222> LOCATION: (4)..(4)
<223> OTHER INFORMATION: Any amino acid or absent

<400> SEQUENCE: 5

Trp Ala Ser Xaa
1

<210> SEQ ID NO 6
```

-continued

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 light chain

<400> SEQUENCE: 6

Lys Gln Ser Tyr His Leu Phe Thr
1               5

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain variable region

<400> SEQUENCE: 7

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Val Lys Leu Lys Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Ile Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Thr Leu
            100                 105                 110

Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain variable region

<400> SEQUENCE: 8

Asp Ile Val Leu Ser Gln Ser Pro Ser Ser Leu Ala Val Ser Ala Gly
1               5                   10                  15

Glu Lys Val Thr Met Arg Cys Lys Ser Ser Gln Ser Leu Leu Asn Ser
                20                  25                  30

Gly Met Arg Lys Ser Phe Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80
```

-continued

```
Ile Ser Ser Val Gln Ala Glu Asp Leu Ala Val Tyr Tyr Cys Lys Gln
                85                  90                  95

Ser Tyr His Leu Phe Thr Phe Gly Ser Gly Thr Lys Leu Glu Ile Lys
            100                 105                 110

<210> SEQ ID NO 9
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: antibody

<400> SEQUENCE: 9

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Val Lys Leu Lys Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Ile Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Thr Leu
            100                 105                 110

Thr Val Ser Ser Gly Gly Gly Gly Ser Gly Gly Gly Ser Gly Gly
        115                 120                 125

Gly Gly Ser Asp Ile Val Leu Ser Gln Ser Pro Ser Ser Leu Ala Val
    130                 135                 140

Ser Ala Gly Glu Lys Val Thr Met Arg Cys Lys Ser Ser Gln Ser Leu
145                 150                 155                 160

Leu Asn Ser Gly Met Arg Lys Ser Phe Leu Ala Trp Tyr Gln Gln Lys
                165                 170                 175

Pro Gly Gln Ser Pro Lys Leu Leu Ile Tyr Trp Ala Ser Thr Arg Glu
            180                 185                 190

Ser Gly Val Pro Asp Arg Phe Thr Gly Ser Gly Ser Gly Thr Asp Phe
        195                 200                 205

Thr Leu Thr Ile Ser Ser Val Gln Ala Glu Asp Leu Ala Val Tyr Tyr
    210                 215                 220

Cys Lys Gln Ser Tyr His Leu Phe Thr Phe Gly Ser Gly Thr Lys Leu
225                 230                 235                 240

Glu Ile Lys Gly Ser Tyr Pro Tyr Asp Val Pro Asp Tyr Ala Gly Ser
                245                 250                 255

His His His His His His
            260

<210> SEQ ID NO 10
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

-continued

```
<223> OTHER INFORMATION: humanized antibody

<400> SEQUENCE: 10

Gln Val Gln Leu Gln Gln Ser Gly Ala Glu Leu Val Lys Pro Gly Ala
1               5               10              15

Ser Val Lys Ile Ser Cys Lys Ala Ser Gly Tyr Thr Phe Thr Asp Tyr
            20              25              30

Tyr Ile Asn Trp Val Lys Leu Ala Pro Gly Gln Gly Leu Glu Trp Ile
        35              40              45

Gly Trp Ile Tyr Pro Gly Ser Gly Asn Thr Lys Tyr Asn Glu Lys Phe
    50              55              60

Lys Gly Lys Ala Thr Leu Thr Ile Asp Thr Ser Ser Ser Thr Ala Tyr
65              70              75              80

Met Gln Leu Ser Ser Leu Thr Ser Glu Asp Thr Ala Val Tyr Phe Cys
            85              90              95

Val Arg Asp Ser Pro Phe Phe Asp Tyr Trp Gly Gln Gly Thr Leu Leu
            100             105             110

Thr Val Ser Ser Gly Gly Gly Gly Ser Gly Gly Gly Gly Ser Gly Gly
        115             120             125

Gly Gly Ser Asp Ile Val Leu Thr Gln Ser Pro Asp Ser Leu Ala Val
    130             135             140

Ser Leu Gly Glu Arg Val Thr Met Asn Cys Lys Ser Ser Gln Ser Leu
145             150             155             160

Leu Asn Ser Gly Met Arg Lys Ser Phe Leu Ala Trp Tyr Gln Gln Lys
            165             170             175

Pro Gly Gln Ser Pro Lys Leu Leu Ile Tyr Trp Ala Ser Thr Arg Glu
            180             185             190

Ser Gly Val Pro Asp Arg Phe Thr Gly Ser Gly Ser Gly Thr Asp Phe
        195             200             205

Thr Leu Thr Ile Ser Ser Val Gln Ala Glu Asp Val Ala Val Tyr Tyr
    210             215             220

Cys Lys Gln Ser Tyr His Leu Phe Thr Phe Gly Ser Gly Thr Lys Leu
225             230             235             240

Glu Ile Lys Gly Ser Tyr Pro Tyr Asp Val Pro Asp Tyr Ala Gly Ser
            245             250             255

His His His His His His
            260
```